US011752326B2

(12) United States Patent
Friedenberg et al.

(10) Patent No.: US 11,752,326 B2
(45) Date of Patent: Sep. 12, 2023

(54) PORTABLE AND WEARABLE HAND-GRASP NEURO-ORTHOSIS

(71) Applicant: Battelle Memorial Institute, Columbus, OH (US)

(72) Inventors: David Friedenberg, Worthington, OH (US); Gaurav Sharma, Columbus, OH (US); Samuel Colachis, Columbus, OH (US); Nicholas Annetta, Columbus, OH (US); Amanda Noonan, Columbus, OH (US)

(73) Assignee: BATTELLE MEMORIAL INSTITUTE, Columbus, OH (US)

( * ) Notice: Subject to any disclaimer, the term of this patent is extended or adjusted under 35 U.S.C. 154(b) by 140 days.

(21) Appl. No.: 17/339,309

(22) Filed: Jun. 4, 2021

(65) Prior Publication Data

US 2021/0379372 A1    Dec. 9, 2021

Related U.S. Application Data

(60) Provisional application No. 63/035,720, filed on Jun. 6, 2020.

(51) Int. Cl.
*A61N 1/04* (2006.01)
*A61N 1/36* (2006.01)
(Continued)

(52) U.S. Cl.
CPC .......... *A61N 1/0452* (2013.01); *A61B 5/0002* (2013.01); *A61B 5/313* (2021.01);
(Continued)

(58) Field of Classification Search
CPC ................ A61N 1/0452; A61N 1/0484; A61N 1/36003; A61N 1/36031; A61B 5/0002;
(Continued)

(56) References Cited

U.S. PATENT DOCUMENTS

2006/0079817 A1* 4/2006 Dewald .............. A63B 21/4019
482/901
2006/0196998 A1* 9/2006 Matteo .................. F16M 11/08
248/921

(Continued)

FOREIGN PATENT DOCUMENTS

WO      2019/043147 A1    3/2019
WO      WO-2019043147 A1 * 3/2019

OTHER PUBLICATIONS

Ting, J et al., A wearable neural interface for detecting and decoding attempted hand movements in a person with tetraplegia, 2019 41st Annual International Conference of the IEEE Engineering in Medicine and Biology Society (EMBC), IEEE, Jul. 23, 2019, pp. 1930-1933 (Year: 2019).*

(Continued)

*Primary Examiner* — Catherine M Voorhees
(74) *Attorney, Agent, or Firm* — Lippes Mathias LLP

(57) ABSTRACT

A portable and wearable hand-grasp neuro-orthosis is configured for use in a home environment to restore volitionally controlled grasp functions for a subject with a cervical spinal cord injury (SCI). The neuro-orthosis may include: a wearable sleeve with electrodes; electronics for operating the wearable sleeve to perform functional electrical stimulation (FES) and electromyography (EMG), the electronics configured for mounting on a wheelchair; and a controller configured for mounting on a wheelchair. The controller controls the electronics to read EMG via the sleeve, decode the read EMG to determine an intent of the user, and operate the electronics to apply FES via the sleeve to implement the intent of the user. The neuro-orthosis may restore hand function. The controller may include a display arranged to be viewed by the subject, for example mounted on an articulated arm attached to the wheelchair.

18 Claims, 18 Drawing Sheets

(51) Int. Cl.
*A61B 5/313* (2021.01)
*A61B 5/00* (2006.01)

(52) U.S. Cl.
CPC .......... *A61B 5/4836* (2013.01); *A61B 5/6894* (2013.01); *A61B 5/744* (2013.01); *A61N 1/0484* (2013.01); *A61N 1/36003* (2013.01); *A61N 1/36031* (2017.08)

(58) Field of Classification Search
CPC .......... A61B 5/313; A61B 5/397; A61B 5/296; A61B 5/389
See application file for complete search history.

(56) References Cited

U.S. PATENT DOCUMENTS

| | | | |
|---|---|---|---|
| 2012/0172682 A1* | 7/2012 | Linderman | G06F 3/015 600/300 |
| 2014/0180361 A1* | 6/2014 | Burdick | A61N 1/36107 607/48 |
| 2015/0012111 A1 | 1/2015 | Contreras-Vidal et al. | |
| 2015/0306373 A1 | 10/2015 | Bouton | |
| 2018/0154132 A1 | 6/2018 | Bouton | |
| 2018/0154133 A1 | 6/2018 | Bouton | |
| 2018/0154140 A1 | 6/2018 | Bouton | |
| 2018/0178008 A1* | 6/2018 | Bouton | A61N 1/36003 |
| 2019/0021883 A1 | 1/2019 | Herr et al. | |
| 2019/0224473 A1 | 7/2019 | Bouton | |
| 2019/0247650 A1 | 8/2019 | Tran | |
| 2020/0206503 A1 | 7/2020 | Ganzer | |
| 2020/0276438 A1 | 9/2020 | Bouton | |
| 2020/0405188 A1 | 12/2020 | Sharma | |
| 2020/0406035 A1 | 12/2020 | Sharma | |
| 2021/0038887 A1 | 2/2021 | Bouton | |

OTHER PUBLICATIONS

Bouton et al., "Restoring cortical control of functional movement in a human with quadriplegia", Nature 533, 247 250, doi:10.1038/nature17435 (2016).

Colachis et al., "Dexterous Control of Seven Functional Hand Movements Using Cortically-Controlled Transcutaneous Muscle Stimulation in a Person With Tetraplegia", Front Neurosci 12, 208, doi:10.3389/fnins.2018.00208 (2018).

Friedenberg et al., "Neuroprosthetic-enabled control of graded arm muscle contraction in a paralyzed human", Scientific Reports 7 (2017).

Sharma et al., "Using an Artificial Neural Bypass to Restore Cortical Control of Rhythmic Movements in a Human with Quadriplegia", Sci Rep 6, 33807, doi:10.1038/srep33807 (2016).

Skomrock et al., "A Characterization of Brain-Computer Interface Performance Trade-Offs Using Support Vector Machines and Deep Neural Networks to Decode Movement Intent", Front Neurosci 12, 763, doi:10.3389/fnins.2018.00763 (2018).

Schwemmer et al., "Meeting brain-computer interface user performance expectations using a deep neural network decoding framework", Nature Medicine 24, 1669-1676, doi:10.1038/s41591-018-0171-y (2018).

Ren et al., "Intramuscular EMG Decomposition Basing on Motor Unit Action Potentials Detection and Superposition Resolution. Front Neurol 9, 2, doi:10.3389/fneur.2018.00002 (2018).

Farina et al., "Principles of Motor Unit Physiology Evolve With Advances in Technology", Physiology (Bethesda) 31, 83-94, doi:10.1152/physiol.00040.2015 (2016).

Bockbrader et al., "Clinically Significant Gains in Skillful Grasp Coordination by an Individual With Tetraplegia Using an Implanted Brain-Computer Interface With Forearm Transcutaneous Muscle Stimulation", Arch Phys Med Rehabil 100, 1201-1217, doi:10.1016/j.apmr.2018.07.445 (2019).

Storn et al., "Differential evolution—a simple and efficient heuristic for global optimization over continuous spaces", Journal of global optimization 11, 341-359 (1997)).

Jordyn Ting, et al, A wearable neural interface for detecting and decoding attempted hand movements in a person with tetraplegia, 2019 41st Annual International Conference of the IEEE Engineering In Medicine and Biology Society (EMBC), IEEE, Jul. 23, 2019.

Nicholas V Annetta, et al, A high Definition Noninvasive Neuromuscular Electrical Stimulation System for Cortical Control of Combinatorial Rotary Hand Movements in a Human With Tetraplegia, IEEE Transactions on Biomedical Engineering, IEEE Service Center, Piscataway, NJ, USA, vol. 66, No. 4, Apr. 1, 2019.

* cited by examiner

PORTABLE AND WEARABLE HAND-GRASP NEURO-ORTHOSIS

This application claims the benefit of U.S. Provisional Application No. 63/035,720 filed Jun. 6, 2020 and titled "PORTABLE AND WEARABLE HAND-GRASP NEURO-ORTHOSIS". U.S. Provisional Application No. 63/035,720 filed Jun. 6, 2020 and titled "PORTABLE AND WEARABLE HAND-GRASP NEURO-ORTHOSIS" is incorporated herein by reference in its entirety.

BACKGROUND

The following relates to neuro-orthosis devices, therapy devices, personal assistant devices, physical therapy devices, physical rehabilitation devices, and to methods of making and using same, and to related arts.

More than 100,000 individuals in the United States currently live without the ability to use their hands because of a cervical spinal cord injury (SCI). An additional 10,000 people develop tetraplegia from SCI each year, with an estimated 225 members of the U.S. military affected annually. Profound disability results from loss of hand function, creating dependence on caregivers for essential activities of daily living (ADLs) (e.g., eating, grooming, dressing). Consequently, loss of hand function often results in loss of independence, transforms relationships, and places the burden of care on family, friends, or paid helpers. Tetraplegia therefore contributes to many serious psychosocial problems suffered by those with cervical SCI, like decreased quality of life, inability to sustain prior socioeconomic roles (e.g., parent, employee, friend), and lack of positive self-management.

Individuals with tetraplegia, and specifically veterans with tetraplegia, have expressed a desire for interventions that enable volitional control of assistive technologies that restore hand function, and thus independence, in daily life. Neuro-orthotic devices that rely on surgically implanted brain computer interfaces (BCI) to control functional electrical stimulation (FES) of muscles have shown promise in this regard, but are not yet available for widespread use. During a recent survey (presented at the SCI2020 conference) of more than 1,800 individuals with SCI and their caregivers, more than 90% responders agreed that they would find treatments to be highly desirable if they are widely available even if they can restore a small amount of function to improve quality of life. Therefore, there is an unmet medical need to develop an easy-to-use, non-surgical neuro-orthosis that is more easily adopted by these paralyzed individuals to improve their quality of life and independence.

Some background references include: U.S. Pub. No. 2021/0038887 titled "SYSTEMS AND METHODS FOR NEURAL BRIDGING OF THE NERVOUS SYSTEM"; U.S. Pub. No. 2020/0406035 titled "CONTROL OF FUNCTIONAL ELECTRICAL STIMULATION USING MOTOR UNIT ACTION POTENTIALS"; U.S. Pub. No. 2020/0405188 titled "NEUROSLEEVE FOR CLOSED LOOP EMG-FES BASED CONTROL OF PATHOLOGICAL TREMORS"; U.S. Pub. No. 2020/0276438 titled "NEURAL SLEEVE FOR NEUROMUSCULAR STIMULATION, SENSING AND RECORDING"; U.S. Pub. No. 2019/0224473 titled "SYSTEMS INCLUDING NEUROMUSCULAR STIMULATION CUFF"; U.S. Pub. No. 2018/0154133 titled "NEURAL SLEEVE FOR NEUROMUSCULAR STIMULATION, SENSING AND RECORDING"; and U.S. Pub. No. 2018/0154132 titled "SYSTEMS INCLUDING NEUROMUSCULAR STIMULATION CUFF".

Some further background references include: Bouton et al., "Restoring cortical control of functional movement in a human with quadriplegia", Nature 533, 247-250, doi: 10.1038/nature17435 (2016); Colachis et al., "Dexterous Control of Seven Functional Hand Movements Using Cortically-Controlled Transcutaneous Muscle Stimulation in a Person With Tetraplegia", Front Neurosci 12, 208, doi: 10.3389/fnins.2018.00208 (2018); Friedenberg et al., "Neuroprosthetic-enabled control of graded arm muscle contraction in a paralyzed human", Scientific Reports 7 (2017); Sharma et al., "Using an Artificial Neural Bypass to Restore Cortical Control of Rhythmic Movements in a Human with Quadriplegia", Sci Rep 6, 33807, doi:10.1038/srep33807 (2016); Skomrock et al., "A Characterization of Brain-Computer Interface Performance Trade-Offs Using Support Vector Machines and Deep Neural Networks to Decode Movement Intent", Front Neurosci 12, 763, doi:10.3389/fnins.2018.00763 (2018); Schwemmer et al., "Meeting brain-computer interface user performance expectations using a deep neural network decoding framework", Nature Medicine 24, 1669-1676, doi:10.1038/s41591-018-0171-y (2018); Ren et al., "Intramuscular EMG Decomposition Basing on Motor Unit Action Potentials Detection and Superposition Resolution. Front Neurol 9, 2, doi:10.3389/fneur.2018.00002 (2018); Stashuk, "EMG signal decomposition: how can it be accomplished and used?", J Electromyogr Kinesiol 11, 151-173 (2001); Farina et al., "Principles of Motor Unit Physiology Evolve With Advances in Technology", Physiology (Bethesda) 31, 83-94, doi:10.1152/physiol.00040.2015 (2016); Holobar et al., "Accurate identification of motor unit discharge patterns from high-density surface EMG and validation with a novel signal-based performance metric", J Neural Eng 11, 016008 (2014); Bockbrader et al., "Clinically Significant Gains in Skillful Grasp Coordination by an Individual With Tetraplegia Using an Implanted Brain-Computer Interface With Forearm Transcutaneous Muscle Stimulation", Arch Phys Med Rehabil 100, 1201-1217, doi:10.1016/j.apmr.2018.07.445 (2019); Storn et al., "Differential evolution—a simple and efficient heuristic for global optimization over continuous spaces", Journal of global optimization 11, 341-359 (1997); Ting et al., "A wearable neural interface for detecting and decoding attempted hand movements in a person with tetraplegia", Proceedings of the IEEE EMBC, Berlin (2019).

Certain improvements are disclosed herein.

BRIEF SUMMARY

In accordance with some illustrative embodiments disclosed herein, a portable and wearable hand-grasp neuro-orthosis is configured for use in a home environment to restore volitionally controlled grasp functions for a subject with a cervical spinal cord injury (SCI). The neuro-orthosis may include: a wearable sleeve with electrodes; electronics for operating the wearable sleeve to perform functional electrical stimulation (FES) and electromyography (EMG), the electronics configured for mounting on a wheelchair; and a controller configured for mounting on a wheelchair and controlling the electronics to read EMG via the sleeve, decode the read EMG to determine an intent of the user, and operate the electronics to apply FES via the sleeve to implement the intent of the user. The neuro-orthosis may in some embodiments restore hand function, for example by decoding the read EMG signals to detect the intent of the user comprising an attempted hand movement. In some embodiments, the electrodes of the sleeve comprise non-invasive high density electromyography (HD-EMG) surface electrodes. In some such embodiments, the electronics include a portable FES stimulator with at least 100 channels. In some embodiments, the controller includes a display arranged to be viewed by the subject and programmed to present an avatar of at least the hand. In some such embodiments, an articulated arm may be attachable to a wheelchair via which the controller including the display is mounted in a position viewable by the subject when the subject is in the wheelchair. In some such embodiments, the controller including the display comprises a tablet computer.

In accordance with some illustrative embodiments disclosed herein, a portable and wearable hand-grasp neuro-orthosis configured for use in a home environment to restore volitionally controlled grasp functions for a subject with a cervical spinal cord injury (SCI) comprises: a wheelchair; a wearable sleeve with electrodes; electronics for operating the wearable sleeve to perform functional electrical stimulation (FES) and electromyography (EMG), the electronics mounted on the wheelchair; and a controller mounted on the wheelchair and controlling the electronics.

In accordance with some illustrative embodiments disclosed herein, a portable and wearable hand-grasp neuro-orthosis method comprises: disposing a subject with a cervical spinal cord injury (SCI) in a wheelchair; disposing a sleeve with electrodes on an arm and/or hand of the subject; via a controller mounted on the wheelchair, controlling electronics mounted on the wheelchair to read electromyography (EMG) of the arm and/or hand of the subject using the sleeve; using the controller mounted on the wheelchair, decoding the read EMG to determine an intent of the subject; and via the controller mounted on the wheelchair, controlling the electronics mounted on the wheelchair to perform functional electrical stimulation (FES) of the arm and/or hand using the sleeve to implement the intent of the subject. Some embodiments further comprise positioning a display of the controller to be viewed by the subject disposed in the wheelchair via an articulated arm attached to the wheelchair.

BRIEF DESCRIPTION OF THE DRAWINGS

Any quantitative dimensions shown in the drawing are to be understood as non-limiting illustrative examples. Unless otherwise indicated, the drawings are not to scale; if any aspect of the drawings is indicated as being to scale, the illustrated scale is to be understood as non-limiting illustrative example.

DETAILED DESCRIPTION

Figure 1:
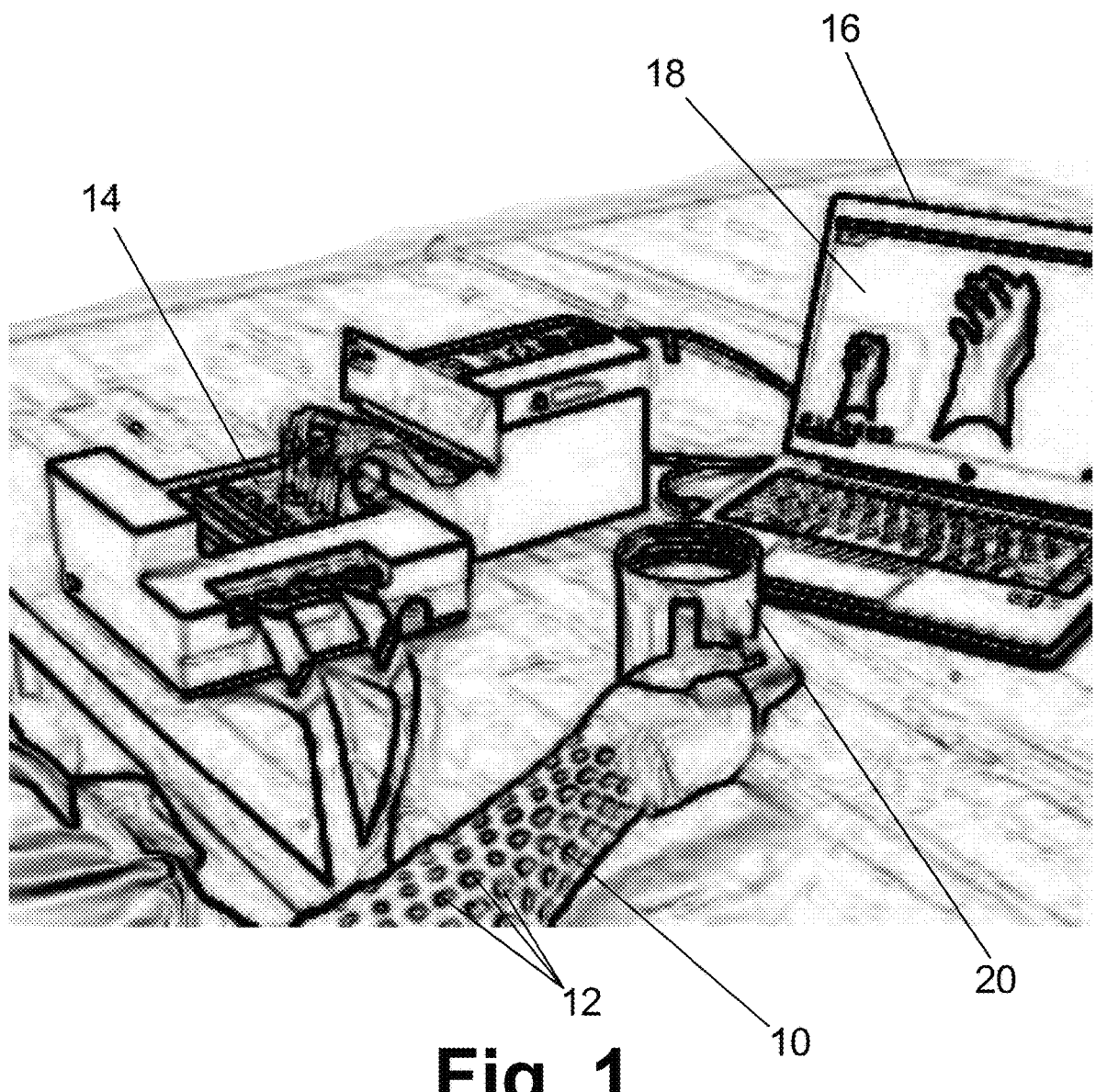
FIG. 1 diagrammatically illustrates a ReGrasp v1 system.

Disclosed herein is a device sometimes referred to herein without loss of generality as ReGrasp, which is based on closed-loop electromyography (EMG)-controlled functional electrical stimulation (FES) of paralyzed muscles to enable hand function. FIG. 1 shows an embodiment of a ReGrasp device that includes a wearable sleeve 10 with electrodes 12 (diagrammatically indicated by markings on the sleeve 10 in FIG. 1, but physically located inside the sleeve 10 in contact with the skin of the wearer), electronics 14 for driving FES and reading EMG, and a controller 16 for controlling the ReGrasp device. In the illustrative example the controller 16 is a notebook computer with a display 18 which in the example task illustrated shows a graphical depiction of an intended action (grasping a cup 20) and a rendering of the actual configuration of the physical hand being controlled. This approach is motivated in part by the finding that residual, sub-movement threshold EMG signals can be measured reliably from the forearm of chronically paralyzed individuals with SCI and stroke using the wearable FES sleeve. This EMG activity can be decoded to discriminate multiple attempted hand movements and then used for continuous control of FES to start and stop multiple desired hand movements in an individual with C5/C6 SCI, by way of nonlimiting illustrative example.

Long-term use of a volitionally controlled FES system has been observed to strengthen muscles in the forearm, resulting in at least partial recovery of hand function in a study participant with C5/C6 SCI. This is significant as it indicates that such a system not only has assistive but also rehabilitative potential to promote at least partial recovery of hand function in chronically paralyzed individuals for whom there has been little or no hope of recovery. Individual motor neuron activity can be reliably tracked in chronic SCI patients using the same wearable sleeve technology. This provides a tool to longitudinally track the strength of the corticospinal connections and their functional effects due to the use of the ReGrasp system as well as to help elucidate the mechanisms of functional improvements.

Prior work has established feasibility of an implanted BCI-controlled FES device (i.e., NeuroLife clinical trial) to reanimate hand grasp, which system restored manual dexterity to a man with C5/C6 tetraplegia after SCI. See Bouton et al., "Restoring cortical control of functional movement in a human with quadriplegia", Nature 533, 247-250, doi: 10.1038/nature17435 (2016); Colachis et al., "Dexterous Control of Seven Functional Hand Movements Using Cortically-Controlled Transcutaneous Muscle Stimulation in a Person With Tetraplegia", Front Neurosci 12, 208, doi: 10.3389/fnins.2018.00208 (2018); Friedenberg et al., "Neuroprosthetic-enabled control of graded arm muscle contraction in a paralyzed human", Scientific Reports 7 (2017); Sharma et al., "Using an Artificial Neural Bypass to Restore Cortical Control of Rhythmic Movements in a Human with Quadriplegia", Sci Rep 6, 33807, doi:10.1038/srep33807 (2016); Skomrock et al., "A Characterization of Brain-Computer Interface Performance Trade-Offs Using Support Vector Machines and Deep Neural Networks to Decode Movement Intent", Front Neurosci 12, 763, doi:10.3389/fnins.2018.00763 (2018). An Artificial Intelligence (AI)-based decoding framework has also been developed and deployed that can sustain high performance for over a year with minimal training. See Schwemmer et al., "Meeting brain-computer interface user performance expectations using a deep neural network decoding framework", Nature Medicine 24, 1669-1676, doi:10.1038/s41591-018-0171-y (2018).

Neurotechnology to reanimate an individual's paralyzed hands can be transformative for reducing disability and enhancing quality of life—but only if end-users find devices intuitive, reliable, functional, and easy to use in the home setting. Embodiments disclosed herein address certain shortcomings in the field of hand-grasp assistive devices that are currently obstacles for adoption, including providing a portable, non-invasive system, improved usability, and functionality and impact on daily life.

To reduce or eliminate portability barriers that would prevent systems from being used in the home, embodiments disclosed herein optimize the hardware and software to deploy a portable and wearable second generation. In one disclosed embodiment, a previous system (referred to as ReGrasp v1) is improved in various ways to provide an improved ReGrasp v2 system. Table 1 provides a comparison of ReGrasp v1 and Regrasp v2. The ReGrasp v2 system is robust enough to be used in the home environment. ReGrasp v 2 provides benefits including: (1) noise immunity in EMG signal detection; (2) automated system calibration and decoding methods; and (3) system integration and user interface design. Further disclosed herein are methods to further decompose EMG signals to extract motor neuron activity and use it as biomarkers to monitor any corticospinal plasticity induced by the long-term use of the ReGrasp v2 device.

TABLE 1

Comparison of ReGrasp v1 system and ReGrasp v2 system

| Component | ReGrasp v1 system (shown in FIG. 1) | ReGrasp v2 system (shown in FIG. 11) |
|---|---|---|
| EMG data acquisition | Intan RHD2000-Series Amplifier Evaluation System (up to 256 channels) | Intan RHD2000-Series Amplifier Evaluation System (up to 256 channels) |
| Computer | Laptop PC | Medical-grade tablet/laptop PC |
| Decoder | Support Vector Machine (SVM) | SVM and/or Deep Neural Network (DNN) |
| Neuromuscular FES | Battelle StimHub portable 160-channel stimulator; up to 160-channel wearable sleeve with conductive hydrogel sheet | Battelle StimHub portable 160-channel stimulator; 160-channel wearable sleeve with conductive hydrogel sheet |
| FES calibration | Anatomy-based trial-and-error method | Anatomy-based trial-and-error method and/or Automated calibration using algorithms |
| Advantages | Good understanding of EMG signals and safety profile; proof-of-concept established for modules and system during IRB-approved able-body and SCI study; 5 years of pilot feasibility and efficacy data for the FES system | Modular; good understanding of EMG signals and interface safety profile; excellent noise immunity, engineered for portability; designed to address end-user priorities for caregiver setup and home use; fully portable and wearable |
| Limitations | Large, not engineered for portability or to address end-user performance criteria | Proof-of-concept in lab setting established for modules; system prototype not yet tested in clinical trial or home setting |

Hereafter, "ReGrasp" is used to specifically refer to the ReGrasp v2 system embodiment, unless otherwise noted.

In a contemplated application, the ReGrasp system is deployed in the clinic with SCI participants (n=5, 1.5 months per participant) to: (a) train participants to use the system to perform basic hand-grasp functions; and (2) perform baseline functional and neurophysiological assessments, including standardized tests of upper limb function and motor neuron activity assessment. We will track changes in standardized clinical tests of hand function throughout the training period. With such training, it is expected that the ReGrasp device can be quickly setup with minimal daily recalibration, is safe to use, can sustain high performance, and participants will be sufficiently trained to successfully manipulate everyday objects they would encounter in their home environment.

In a contemplated application, the ReGrasp system is used in the home of a person with SCI, for example in their own kitchen, bathroom, and bedroom instead of the artificial environment of the lab. In an embodiment, a wearable, take-home ReGrasp device provides significant improvements in functional independence and quality of life for individuals with tetraplegia.

The ReGrasp system addresses unmet needs identified in both the Rehabilitation (primary) and Psychosocial (secondary) SCI Research Program Focus Areas by providing a translational non-surgical neuro-orthosis device to restore hand function to those with paralysis. By restoring lost hand function, the ReGrasp device can help relieve the impact of SCI, improve quality of life of survivors, and reduce burden on caregivers.

In a contemplated embodiment, ReGrasp comprises a fully wearable and portable non-invasive system that not only reanimates hand grasp for those with paralysis but has been designed to meet end-user priorities. Some such embodiments establish motor unit (MU) and EMG-based neurophysiological correlates of functional improvements which are expected due to the use of the device. This is expected to provide a broader understanding of the effects of assistive devices on corticospinal plasticity. The ReGrasp system is a platform device which in some contemplated embodiments comprises a device configuration that is not only simpler (e.g., reduced number of electrodes and their optimal location, use and training procedures) but also more robust (e.g., improved signal processing and decoding algorithms).

FES devices evoke grips strong enough to hold and manipulate objects, demonstrating a particularly useful utility for individuals with mid-cervical SCI who lack the ability grasp objects, and thus, require assistance for activities of daily living (ADLs). In addition to improving function and independence, upper limb FES confers additional health benefits to those who are paralyzed, including muscle conditioning to increase contractile force, preservation of joint range of motion, prevention of contractures, reduction of spasticity, and the potential for promoting central nervous system plasticity, bone mineralization, and cardiopulmonary conditioning.

In previous work, both transcutaneous and implantable FES systems have been tested successfully in people with SCI under a variety of control mechanisms: myoelectric, voice, switch, position sensors, electro-oculography or electroencephalography (EEG), electrocorticography (ECoG), and intracortical microelectrode array (MEA) recording. Unfortunately, no single system has simultaneously delivered naturalistic grasp speed, force, and dexterity paired with an intuitive, user-friendly, and high degree-of-freedom (DoF) control mechanism that people can use in their homes. Advances in portable high-definition EMG-based neuro-orthotic systems for delivering real-time FES have the potential to overcome these barriers, so that the control system of the disclosed ReGrasp system is expected to provide the benefits including at least: being non-invasive, providing intuitive control, providing fast response time, being a low-cost system, being easy to use, and having rapid setup time.

In previous work, muscle interfacing with either implanted or non-invasive systems to record EMG activity to record intent has been extensively investigated for bionic prostheses control. EMG recordings provide indirect neural information, since muscle electrical activity is generated by the neural activation from peripheral nerves. Mono-dimensional arrays were initially proposed and then extended to bi-dimensional grids. These systems have been referred to as high-density surface EMG (HD-EMG) due to the relatively high number of electrodes and close separation between electrodes. HD-EMG provides a spatial representation of the electrical activity generated by the underlying excitable tissues and is used widely in a variety of different applications from basic neuroscience to kinesiology and rehabilitation, as well as for control of human-machine interfaces.

EMG-based neuro-orthotics for delivering real-time FES, therefore, have the potential to restore volitional hand function in individuals with chronic paralysis. Indeed, EMG-controlled FES of hand muscles has been investigated in previous studies as a therapeutic modality for post-stroke rehabilitation. In these studies, EMG activity was recorded from the forearm of individuals with chronic hemiplegia after stroke and then used to trigger or control FES of forearm muscles to evoke finger and wrist extension. Furthermore, researchers also showed that, in just 5 months of intervention, the use of EMG-controlled FES in individuals with stroke-related hemiplegia can lead to cortical reorganization that is correlated with improvements in hand function. These results point to the beneficial effects of sensorymotor integration due to the use EMG-FES for neurological recovery and functional improvements even in chronically paralyzed individuals.

Recently, an EMG-based orthotic for upper limb reanimation was demonstrated in an individual with C5/C6 American Spinal Injury Association (ASIA) B SCI. In this study, EMG activity was recorded below the level of SCI (i.e., from patient's foot) and was then used to control an implanted FES system in the hand. While promising, this solution utilizes a non-intuitive mapping between thought and action that can be awkward, inconvenient, and cognitively demanding. Therefore, synergistic EMG-based neuro-orthotics, where EMG activity is leveraged from the muscles that are targeted by FES, are preferable because they are intuitive, non-invasive, and relatively inexpensive. However, reliable extraction of meaningful EMG from upper limb muscles of chronically paralyzed cervical-level SCI patients is difficult, and there are technical challenges in performing real-time, simultaneous EMG extraction, decoding and FES on nearby electrodes in a high-density electrode setup in the home environment. Previous work has shown that measurable EMG of the forearm muscles can be extracted using the high-density sleeve electrode array during attempted finger and hand movements and was decodable at high accuracy in two participants with chronic C5/C6 SCI. These findings evidence that an EMG-based hand-grasp neuro-orthotic can help individuals with chronic SCI regain hand function.

During muscle contraction, MUs are recruited and generate action potential (AP) trains. Information regarding MU AP activity is embedded in EMG signals and can be decomposed using algorithms that can identify MU AP characteristics based on wave shape and firing patterns. See Ren et al., "Intramuscular EMG Decomposition Basing on Motor Unit Action Potentials Detection and Superposition Resolution. Front Neurol 9, 2, doi:10.3389/fneur.2018.00002 (2018); Stashuk, "EMG signal decomposition: how can it be accomplished and used?", J Electromyogr Kinesiol 11, 151-173 (2001). Imperial College London has shown that HD-EMG signals can be decomposed into constituent MU APs. See Farina et al., "Principles of Motor Unit Physiology Evolve With Advances in Technology", Physiology (Bethesda) 31, 83-94, doi:10.1152/physiol.00040.2015 (2016) This led to development of methods of blind source separation that can identify discharge timings of a large number of individual motor neurons from HD-EMG recordings. See Holobar et al., "Accurate identification of motor unit discharge patterns from high-density surface EMG and validation with a novel signal-based performance metric", J Neural Eng 11, 016008 (2014). These methods have opened a window into studying large pools of motor neurons in the spinal cord in humans and transformed EMG from a peripheral measure of muscle electrical activity to a neural recording system.

Therefore, in addition to opening new avenues for developing neural interfacing technologies, HD-EMG decomposition into MU activity has also provided a new tool to enable basic scientific investigations of the behavior of motor neurons during natural tasks and for detecting the activity of a relatively large fraction of the target motor neuron populations. Indeed, through decomposition of non-invasive HD-EMG data, motor neurons are the only neural cells in humans in which discharge timings can be exactly identified without the need for a surgical intervention.

Notably, if each of the 100,000 Americans with tetraplegia regained use of their hands and could perform self-care, this would produce a savings of $4 billion per year in supportive care costs alone. The ReGrasp system is designed to overcome other barriers to translation for home use through human-centric system design centered around end-user and performance expectations.

Survey responses have been evaluated of potential users with SCI5-7 to better define the barriers to translation of our proposed device from the laboratory to home use, identify end-user design priorities, and translate these barriers and priorities into ReGrasp system requirements. In a survey of 57 veterans with SCI6, it was found that non-invasiveness, daily setup time, independent operation, cost, number of functions provided, and response time were all rated as "very important" design characteristics. In a different survey of 40 individuals with SCI, the functionality provided and setup time for a neuroprosthesis were identified as the top priorities. Speed, accuracy, electrode type, standby reliability, training location, and training time were also deemed important.

There is consensus across several surveys that restoration of hand function is a top priority for individuals with SCI that would impact quality of life. In addition, technological improvements in portability, daily setup and take-down times, decoder and FES calibration, ease-of-use, generalizability and durability are expected to facilitate deployment of these devices in an end-user's home.

Figure 2:
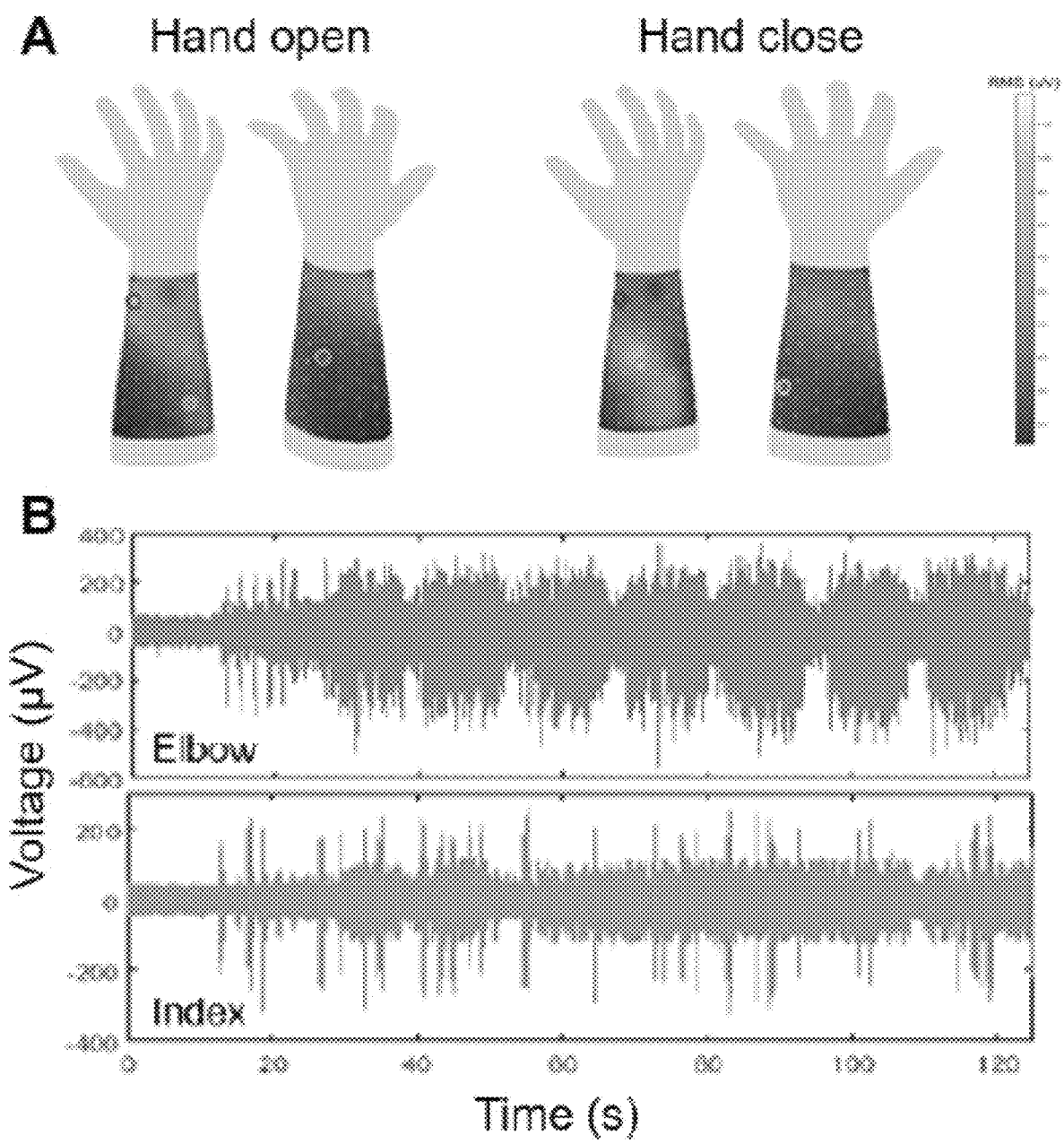
FIG. 2 diagrammatically illustrates volitional EMG activity heatmaps (part A) and EMG activity (part B).
Figure 3:
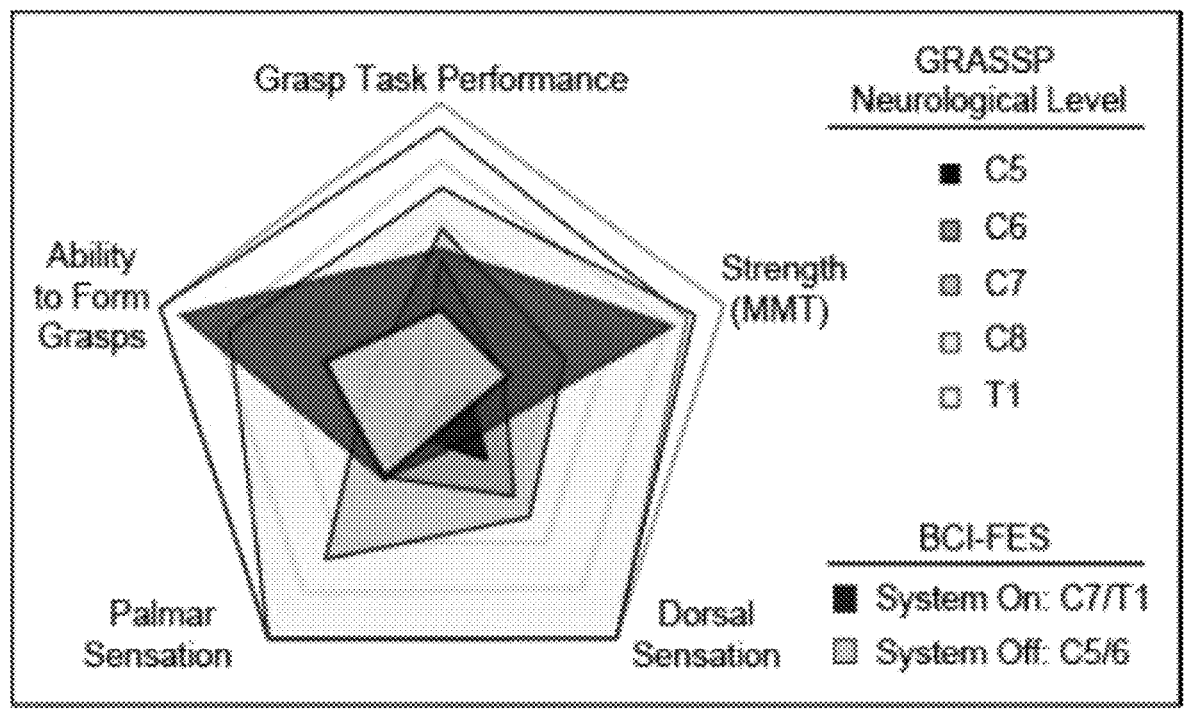
FIG. 3 diagrammatically illustrates functional neurologic level in GRASSP testing.
Figure 4:
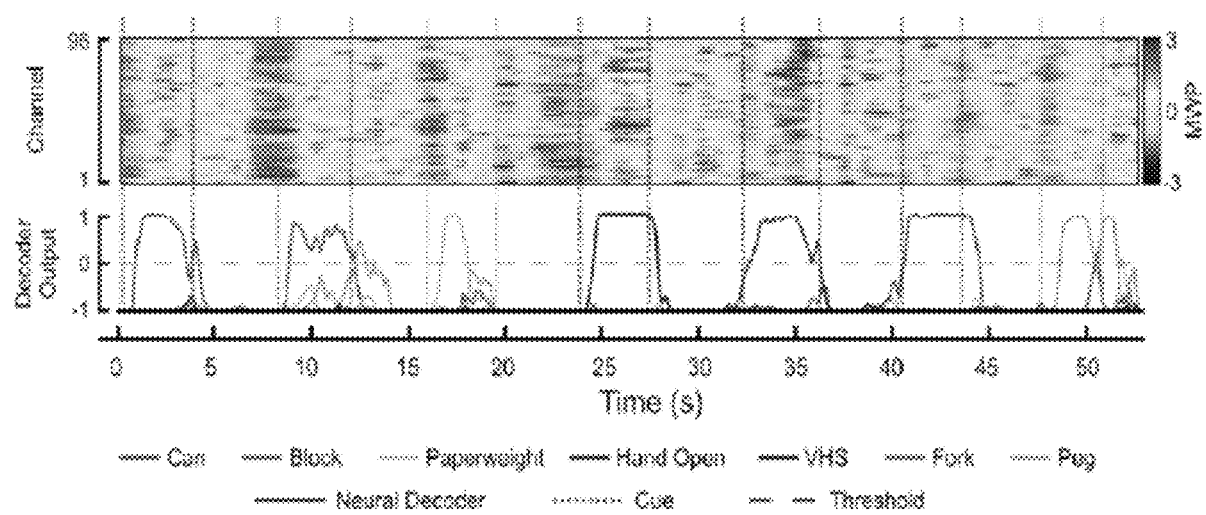
FIG. 4 diagrammatically illustrates a heat map of neural activity (top) and Support Vector Machine (SVM) decoder outputs (bottom) for six Grasp and Release Test (GRT) object grips and hand open.
Figure 5:
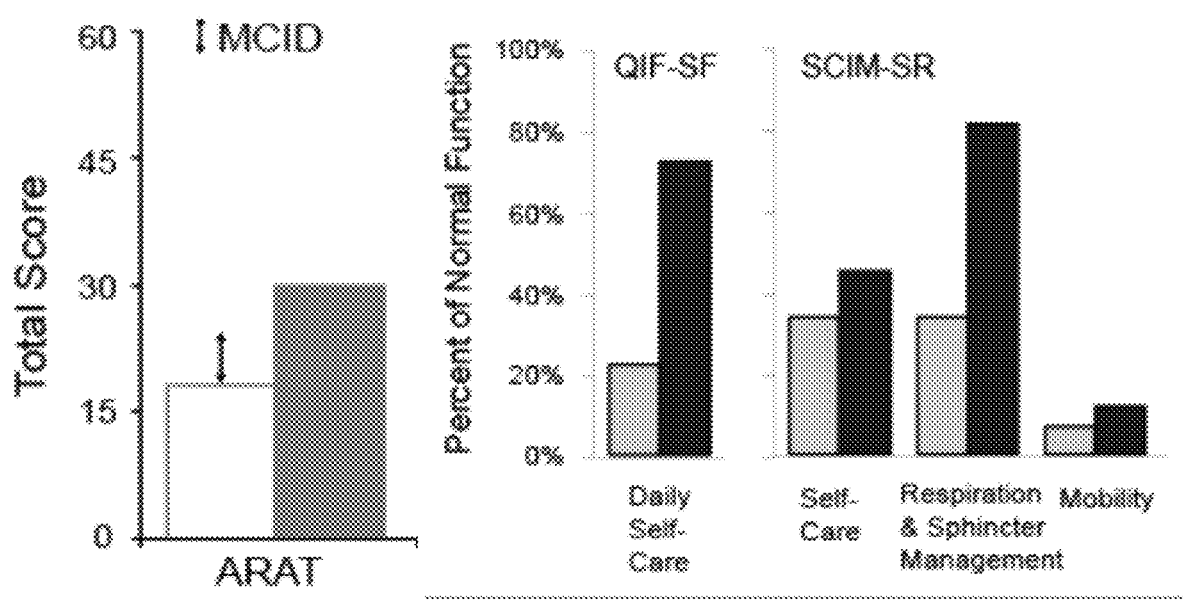
FIG. 5 diagrammatically illustrates various metrics of use of the NeuroLife system as described herein.

The NeuroLife clinical trial demonstrated safety and feasibility of a BCI-FES system to reanimate hand grasp after C5/C6 SCI. See Bouton et al., "Restoring cortical control of functional movement in a human with quadriplegia", Nature 533, 247-250, doi:10.1038/nature17435 (2016). This system recorded neural activity from the motor cortex via a surgically implanted 96-channel Utah array, applied real-time signal processing and decoding to the neural activity, and returned voluntary control of the participant's forearm muscles through a custom-built, high-resolution, non-invasive FES cuff. This proof-of-concept, Phase I, investigational device trial (NCT01997125) was U.S. Food and Drug Administration (FDA) IDE-approved for 12 months, but due to its success was subsequently extended to a 60-month duration through FDA and Institutional Review Board (IRB) amendments. The first participant enrolled in this trial was a 22-year-old male with chronic, complete, C5/C6 ASIA A, non-spastic tetraplegia due to cervical SCI 3 years prior. Using this system, movement was restored to the participant's paralyzed right wrist and hand by linking FES muscle activation in real time with motor cortex multi-unit activity underlying his intent to move. Using the system, he was able to perform dexterous hand grasps and complex, compound hand movements. This study demonstrated that the NeuroLife system can enable continuous cortical control of isolated finger movements, six wrist and hand motions, and object manipulation with palmar and lateral pinch grasp. See FIG. 2, which shows (part A) Volitional EMG activity heatmap recorded using from an individual with stroke attempting hand open and close movements, and (part B) EMG activity from a single electrode recorded during executed elbow flexion and extension trials (top) and attempted index finger flexion and extension trials (bottom) by an individual with C5/C6 SCI. Additionally, the study showed that the Graded Redefined Assessment of Strength, Sensation, and Prehension (GRASSP) functional neurologic level of the participant improved from C5/C6 to C7/T1 when using the system. See FIG. 3, which shows functional neurologic level clinically improved from C5/C6 to C7/T1 (dark gray) on GRASSP testing, indicating greater independence using the NeuroLife system. Notably, most individuals with C7/T1 level injuries can live independently, while those at the C5/C6 level typically cannot. In subsequent studies, the functionality of the NeuroLife system was further extended by improving the hardware and software and showed that the participant could use the system to control seven distinct hand movements to manipulate Grasp and Release Test (GRT) objects with naturalistic grasps in real time with high (>95%) accuracy. See Colachis et al., "Dexterous Control of Seven Functional Hand Movements Using Cortically-Controlled Transcutaneous Muscle Stimulation in a Person With Tetraplegia", Front Neurosci 12, 208, doi:10.3389/fnins.2018.00208 (2018). As an example, FIG. 4 shows a heat map of the neural activity and Support Vector Machine (SVM) decoder outputs (bottom of FIG. 4) for the six GRT object grips and hand open. This study also showed that the participant could control both discrete as well as rhythmic movements and could volitionally modulate the FES amplitude to grade his muscle contraction. In addition, the study participant made and sustained clinically significant gains in manual dexterity on the Action Research and Arm Test (ARAT) for 4.5 years post-implant. He demonstrated naturalistic speed and dexterity and stated that, if he could use a volitionally controlled FES system at home, he expected to improve independence for self-care ADLs. See Bockbrader et al., "Clinically Significant Gains in Skillful Grasp Coordination by an Individual With Tetraplegia Using an Implanted Brain-Computer Interface With Forearm Transcutaneous Muscle Stimulation", Arch Phys Med Rehabil 100, 1201-1217, doi:10.1016/j.apmr.2018.07.445 (2019). FIG. 5 shows use of the NeuroLife system (right bar of the MCID plot of FIG. 5) significantly improved manual dexterity over the baseline (left bar of the MCID plot of FIG. 5). The user anticipated device use in the home (black bars of the righthand plot of FIG. 5) would improve his ability to perform ADLs over the baseline (gray bars of the righthand plot of FIG. 5). Functionality was further extended to decode simultaneous movement intentions (e.g., grip, pronation) and enable interleaved stimulation of distinct FES muscle activation patterns. The user then could select hand and forearm states independently and dynamically adjust evoked FES states in real time to maintain grip while transitioning from pronation through supination.

In a related study, a 41-year-old female veteran was enrolled with chronic, C4 ASIA A, spastic tetraplegia due to cervical SCI 9 years prior. She used the FES component of the ReGrasp system under verbal control on her dominant arm. Although she initially needed a mobile arm support to compensate for shoulder weakness, had more challenging forearm anatomy for FES (i.e., shorter, thinner, more atrophied forearms), and required forearm muscle conditioning to develop grasp strength, she has been able to achieve functional palmar, tip-to-tip, and lateral grips using FES.

These studies reveal the promise of using a volitionally controlled FES system for enabling naturalistic, skillful, high DoF grasp coordination for individuals with tetraplegia after SCI. Potential end-users want a system they can use at home and have an expectation that it would improve independence and quality of life. Patient surveys and end-user experience with the device have helped identify ways in which the system should be redesigned to overcome barriers to practical use for ADLs in the home. A contemplated embodiment (e.g. FIG. 11) provides a portable, wearable ReGrasp system engineered for home use and replace the invasive implanted array with the non-invasive EMG.

In a contemplated embodiment, deep neural network (DNN) based decoding strategies are employed to improve system performance to meet end-user performance expectations for high accuracy, minimal daily setup time, rapid response times, and multifunctionality.

Figure 6:
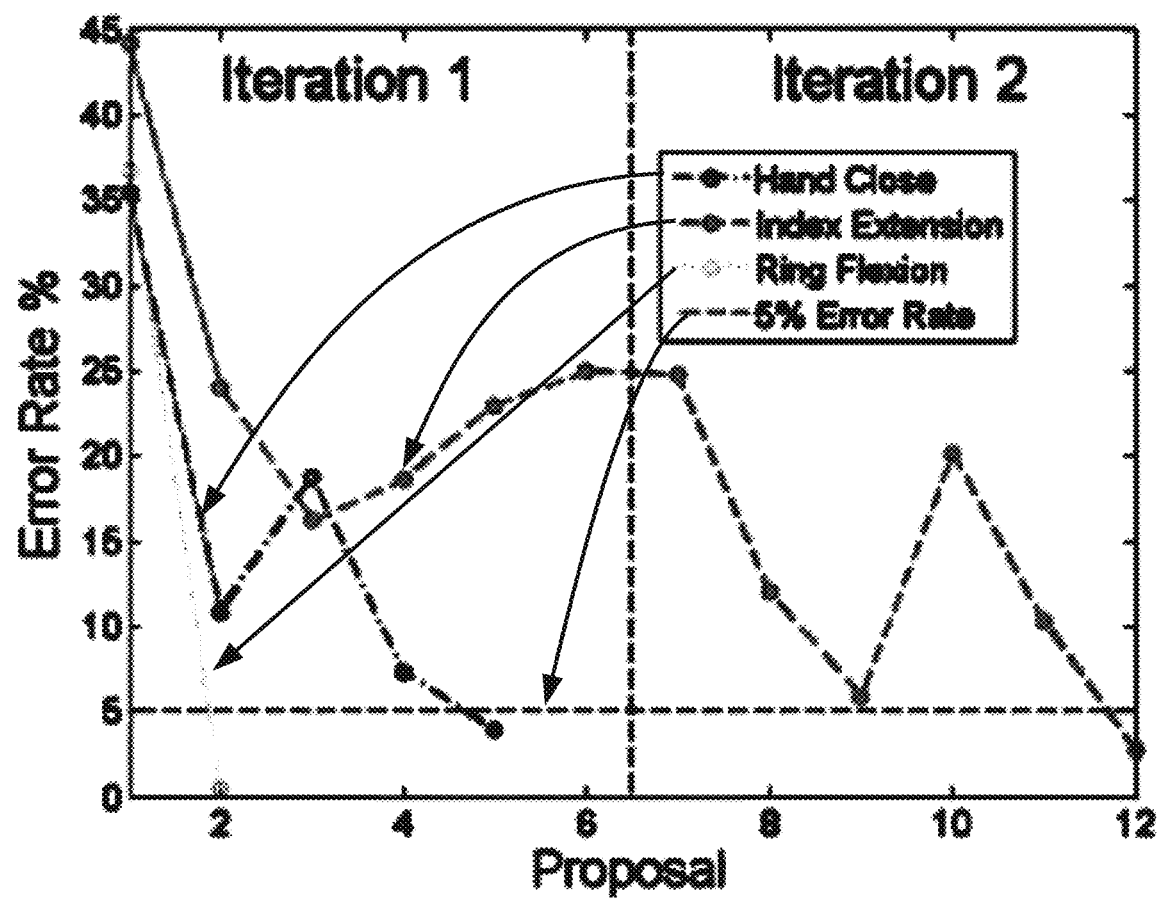
FIG. 6 diagrammatically illustrates an example of auto-mated electrode-to-muscle mapping calibration in able-bod-ied participant.

In an IRB-approved study with able-bodied participants, a differential evolution (DE) optimization algorithm (see Storn et al., "Differential evolution—a simple and efficient heuristic for global optimization over continuous spaces", Journal of global optimization 11, 341-359 (1997)) was used initialized with previously successful FES patterns to calibrate the electrode-to-muscle mapping necessary for evoking three desired hand states in 15 minutes. Feedback from the bend sensors and accelerometer-enabled sleeve was used to replace visual feedback from a technician and to guide the algorithm. FIG. 6 shows an example of automated electrode-to-muscle mapping in able-bodied participant. After 12 proposals (~15 minutes), the algorithm found acceptable stimulation parameters for three movements. This method streamlines FES calibration and eliminates the need for a technician with specialized knowledge of forearm anatomy.

Figure 7:
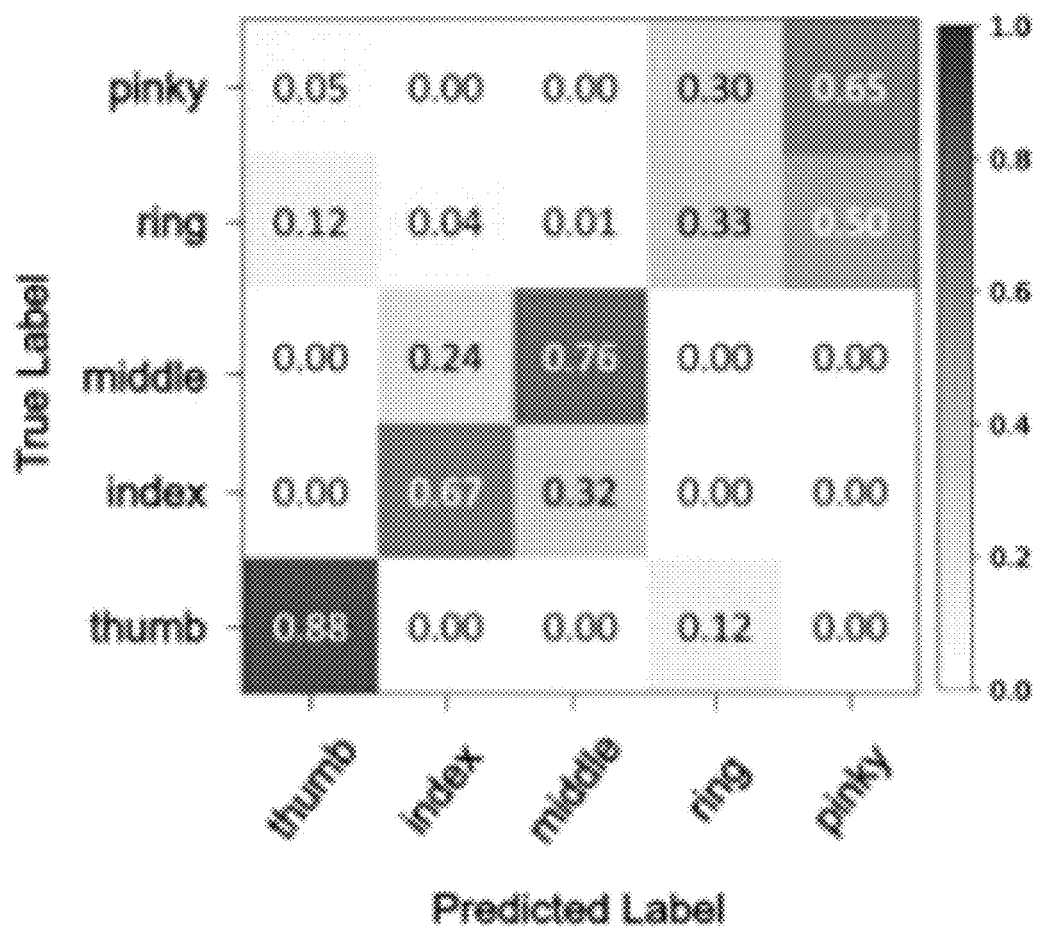
FIG. 7 diagrammatically illustrates an example of detectable and discriminable EMG activity from individuals with SCI for five-digit tasks.

As part of the referenced NeuroLife and CRS studies, we have also demonstrated that the ReGrasp sleeve can be used for detecting and decoding signals from spared MUs in the forearms of people with tetraplegia after SCI. Two participants with C5/C6 SCI from the NeuroLife and CRS clinical trials and who have intracortical MEA participated in this study. The wearable ReGrasp sleeve with 150 electrodes was used to map the EMG activity of forearm muscles during a wide range of voluntary attempted hand movements. The first participant, with C5/C6 ASIA B chronic tetraplegia after SCI, followed cues displayed on a computer and attempted five different finger movements. Despite exhibiting no overt finger motion, EMG signals were detectable for attempted movements of individual digits and were highly discriminable. See Ting et al., "A wearable neural interface for detecting and decoding attempted hand movements in a person with tetraplegia", Proceedings of the IEEE EMBC, Berlin (2019). FIG. 7 shows an example of detectable and discriminable EMG activity from individuals with SCI. As seen in FIG. 7, classification of five-digit tasks in an individual with SCI shows high classification accuracy for several movements.

We are currently conducting an IRB-approved study to investigate the ReGrasp v1 system in participants with SCI (refer to FIG. 1 illustrating the ReGrasp v1 system). As part of this study, we recruited an individual with C5/C6 ASIA A motor complete SCI as the first participant. The prototype ReGrasp v1 system being used in this study was designed and built under Battelle's International Organization for Standardization (ISO) 13485 certified Quality Management System (QMS). This version of the system uses our first generation 160-channel portable stimulator (StimHub), an Intan RHD2000-Series Amplifier Evaluation System (up to 256 channels), our first generation 150-electrode wearable FES sleeve used with a hydrogel sheet as a conduction enhancer between the electrodes and skin, a custom adapter board, and a laptop. The adapter board enables each electrode of the sleeve to be connected in hardware to any stimulator channel or any EMG amplifier channel. The Intan hardware and the portable stimulator are both battery powered. A custom graphical user interface runs on the laptop, which enables the operator to adjust EMG, stimulation, and training parameters (e.g. filtering frequency, stimulation patterns, cue times).

Figure 8:
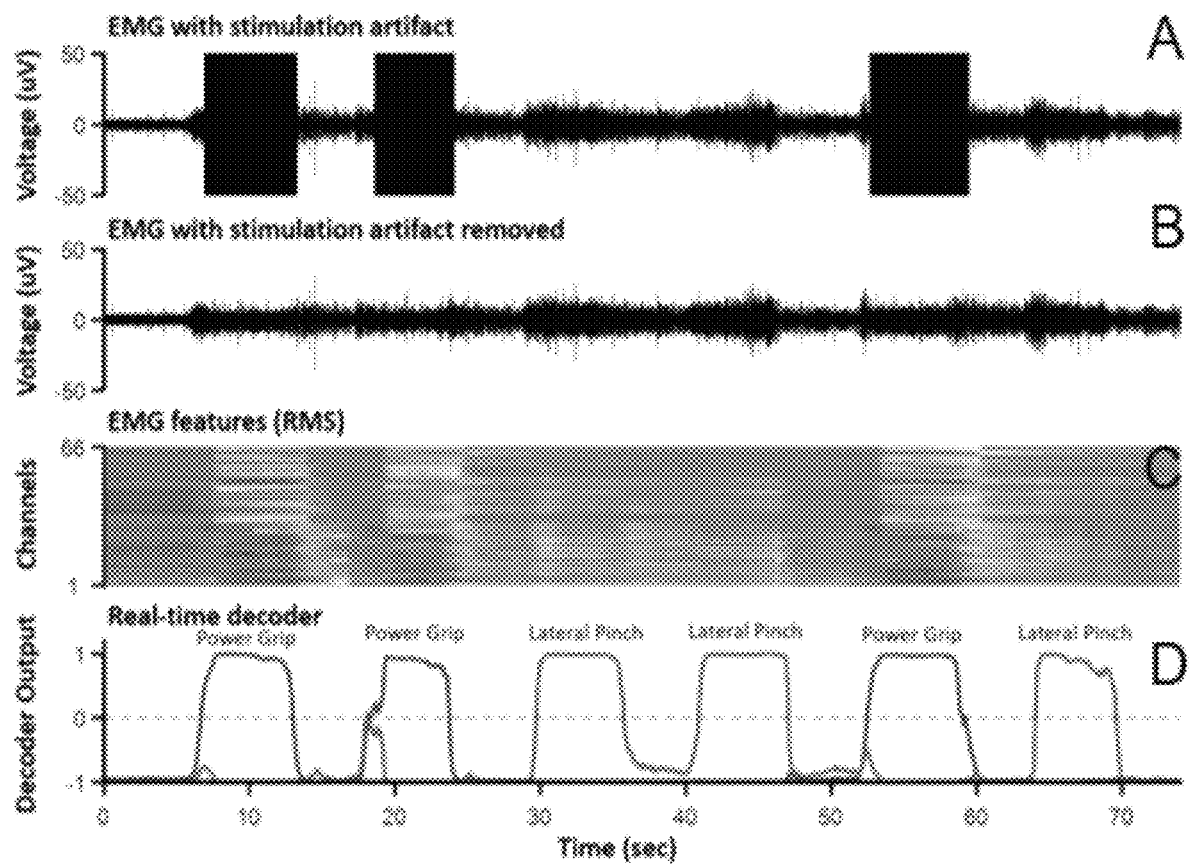
FIG. 8 diagrammatically illustrates various data collected during real-time EMG-controlled FES by an individual with SCI as described herein.

We have shown that the study participant can use the ReGrasp v1 system to perform EMG-controlled FES. FIG. 8 presents real-time EMG-controlled FES by an individual with SCI. FIG. 8(A) presents raw EMG signals that were collected from an SCI participant using the ReGrasp v1 system and attempting two hand/arm movements—hand pronation with finger flexion ("power grip") and lateral pinch—movements that he has difficulty performing on his own. FIG. 8(B) shows results of a blanking method that was used to remove FES-induced artifacts. FIG. 8(C) presents results of processed signals that were then fed as an input into a SVM-based decoding algorithm to detect attempted movement out of two available movements and rest. FIG. 8(D) presents results in which the decoded movement was then used to control FES to volitionally start and stop the power grip movement. Decoder outputs above the dashed line in FIG. 8(D) triggers the FES. Cue timing is indicated by the top-most horizontal line segments.

In some embodiments, a ReGrasp system training protocol is disclosed. In this training protocol, participants follow along with a virtual hand on the screen that indicates which movement they should attempt and when to start and stop. EMG data are collected across multiple repetitions of each movement and used to build a decoder. After a decoder is built, when the participant attempts a movement, the decoder determines which movement is being attempted and stimulates with the specified pattern to evoke the attempted movement. Advantageously, by this method an individual with chronic paralysis due to SCI can regain volitional and naturalistic control of his hand to start/stop movements on demand using a completely non-invasive wearable neuro-orthotic system.

Figure 9:
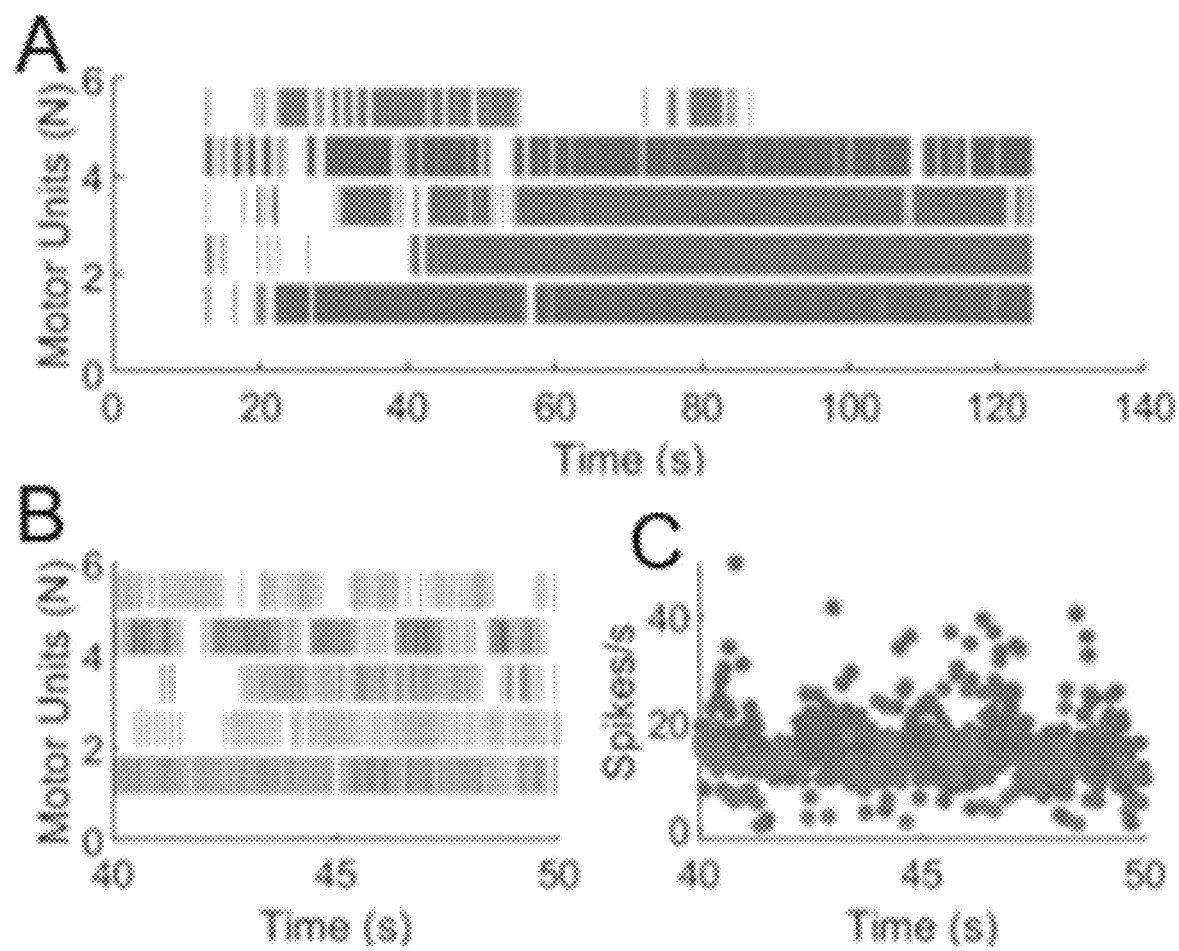
FIG. 9 diagrammatically illustrates extracted MU activity from SCI participant as described herein.

We further performed MU decomposition on the EMG data collected from the same subject and were able to identify the activity of more than 30 motor neurons, active specifically during rotation, pronation of the wrist (4 units), and flexion of the elbow joint (7 units), and during attempted movements of individual hand digits (1-5 units). See Ting et al., "A wearable neural interface for detecting and decoding attempted hand movements in a person with tetraplegia", Proceedings of the IEEE EMBC, Berlin (2019). FIG. 9 shows extracted MU activity from SCI participant. FIG. 9(A) shows a raster plot of the identified MUs as the participant attempted Index flexion. The lower panel shows 10 seconds of firing activity for both the spike instances (FIG. 9(B)) and spikes per second (FIG. 9(C)). In addition, we performed a neural connectivity analysis based on the power of the common oscillations of the identified motor neurons in the delta (~5 Hz), alpha (6-12 Hz), and beta bands (15-30 Hz). This analysis showed clear common synaptic inputs to the identified motor neurons in all the analyzed frequency bands. In some contemplated embodiments, this framework is usable to study reorganization and recovery of spinal networks in our study participants to assess their progress as they use the ReGrasp system in-clinic and then at home.

Disclosed herein are embodiments that address unmet needs of individuals with tetraplegia after SCI. These needs have been identified in the Rehabilitation and Psychosocial SCI Research Program Focus Areas, in multiple patient and veterans' surveys, and by our study participants. In particular, individuals with SCI want interventions that restore function to their paralyzed hands, facilitate independence in their daily life, and enhance quality of life for themselves and their caregivers. New developments in neurotechnology make it possible to test the safety, feasibility, usability, and efficacy of a novel, fully wearable non-invasive ReGrasp system designed around end-user priorities and for home use. The disclosed embodiments are expected to be broadly applicable to those with paralysis, especially because insights gained from testing each of the modular components of this investigational system can be applied to other settings (e.g., control of devices other than FES, simultaneous FES control of both hands, FES for lower limbs for ambulation, therapeutic FES to drive motor recovery in the acute phase after injury). In addition, deeper insight are expected to be provided into relationships between corticospinal plasticity and FES-related rehab, psychosocial function, self-efficacy, and ability to maximize residual upper limb function through neurotechnology.

In one embodiment, the IRB-approved ReGrasp v1 system is modified to deploy it for in-home use. In this embodiment, the ReGrasp v2 system will includes:

A high-definition EMG signal capture system that is fully integrated into the sleeve design (see FIG. 10) and that records and digitizes the EMG signals close to the source;

A portable 160-channel FES stimulator (StimHub) that sends the stimulation pulses back to the sleeve to stimulate the muscles in the forearm to evoke the intended movements of the hand.

A laptop/tablet-based user interface as well as an integrated control system and hardware (e.g., analog switches) between the FES electrodes and the EMG amplifiers, controlled by the StimHub's sync output, that automatically disconnects the amplifiers from the electrodes immediately before the stimulation pulse and reconnects them immediately after the stimulation pulse. This setup will help to further reduce the stimulation artifact and will protect the amplifiers from being damaged by the high voltage of the stimulation.

Figure 10:
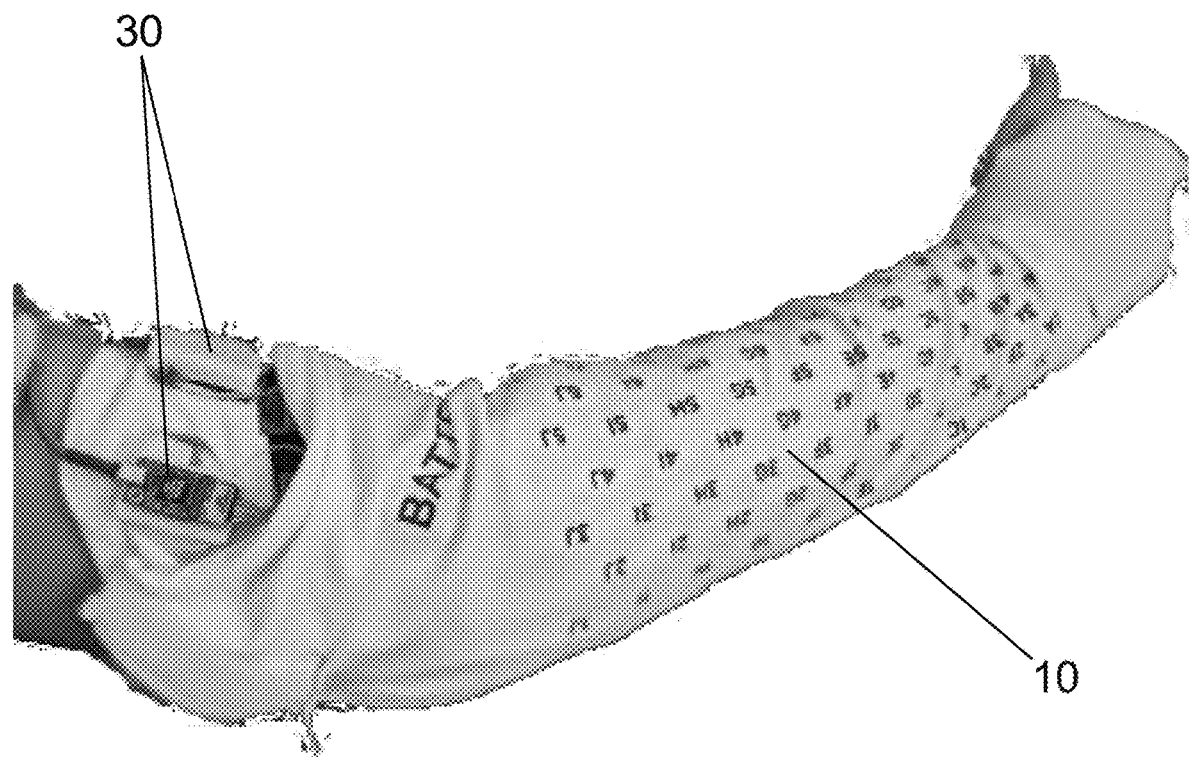
FIG. 10 diagrammatically illustrates a high-definition EMG signal capture system that is fully integrated into the sleeve design and that records and digitizes the EMG signals close to the source.

FIG. 10 shows a version of the ReGrasp sleeve with integrated EMG amplifiers 30. This improved sleeve is currently under investigation in able body participants.

Modifications are also disclosed to address the system's safety, execute verification and acceptance testing, and update or create the associated logistical support documentation and tools needed to support in-home use. Safety and verification tests are suitably determined based on hazard analyses of the system and its component parts using Battelle's ISO 13485:2016 certified QMS. The ReGrasp v1 system (shown in FIG. 1), is presently being tested in the clinic and will be used at the beginning of Aim 2 to start in-clinic experiments with the initial study participants. It is our expectation that at the end of Aim 1.1, we will have built, tested, and gained IRB approval for the take-home version of the ReGrasp system (FIG. 11, also referred to herein as the ReGrasp v2 system).

Figure 11:
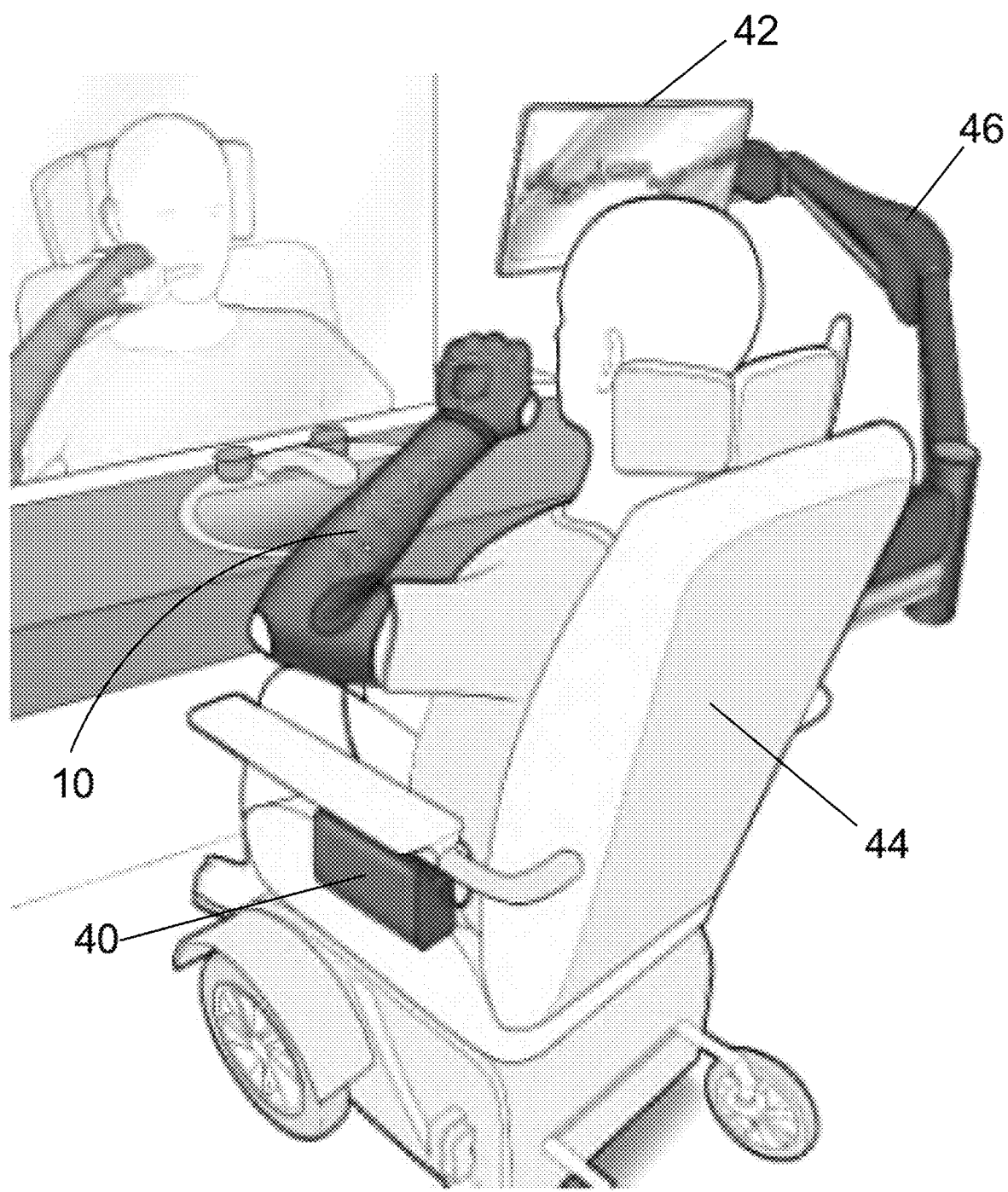
FIG. 11 diagrammatically illustrates a ReGrasp v2 system.

FIG. 11 shows the ReGrasp v2 system being used in a participant's home. The system shows the wearable sleeve 10 with integrated EMG amplifiers (as shown in FIG. 10) and a wheelchair-mounted FES/EMG electronics 40 and tablet PC based GUI controller 42. Instead of the illustrative tablet computer, the controller 42 may be implemented by an otherwise configured electronic processor in wired or wireless (e.g. Bluetooth™) communication with the FES/EMG electronics 40. Illustrative FIG. 11 shows the FES/EMG electronics 40 mounted on a wheelchair comprising a powerchair 44, and the tablet-based controller 42 is mounted on an articulated arm 46 to enable it to be positioned for easy viewing by the subject while performing a task.

In further contemplated embodiments, methods are provided to enable noise immunity in EMG signals, identify optimal features from the EMG data, develop decoding algorithms that can enable real-time control with high accuracy and minimal training, and optionally to develop procedures for automated system calibration. The development of these methods may be conducted with preliminary testing on able-body volunteers prior to deployment in the clinical trial.

In some contemplated embodiments, algorithms are provided for real-time decoding of EMG signals to determine the user's motor intention, which will then trigger the StimHub 40 to deliver the FES pattern for evoking the intended movement. Our initial decoding approach will use time-domain (TD) features extracted from 50 ms epochs of the myoelectric signal. The EMG features are derived from muscle activation patterns, and we have observed these signals in two SCI subjects despite the underlying muscles being paralyzed. These control signals will then be classified, for example using an SVM type classifier due to its simplicity of implementation and ease-of-training. The classified signals will then be used to dynamically activate stimulation patterns to evoke the desired hand/arm movement. Testing on volunteers is contemplated to develop the optimal combination of features and classifier for performance of the myoelectric controller. One contemplated approach uses wavelet decomposition for feature extraction and comparison can be made of the TD features to wavelet-based features as well as other features commonly used in EMG decoding. In addition, various methods for filtering data artifacts caused by the stimulation system are contemplated. As a further contemplated variant, alternative classifiers such as a Linear Discriminant Analysis can be employed. We have made significant progress in developing and testing suitable signal processing, artifact removal, and decoding algorithms as part of an IRB-approved study in a participant with C5/C6 SCI, using the ReGrasp v1 system. As yet further contemplated embodiments, deep learning methods can be used for decoding as we have pioneered methods to directly address user requirements via deep learning decoders in a related application. See Schwemmer et al., "Meeting brain-computer interface user performance expectations using a deep neural network decoding framework", *Nature Medicine* 24, 1669-1676, doi:10.1038/s41591-018-0171-y (2018); Skomrock et al., "A Characterization of Brain-Computer Interface Performance Trade-Offs Using Support Vector Machines and Deep Neural Networks to Decode Movement Intent", Front Neurosci 12, 763, doi:10.3389/fnins.2018.00763 (2018).

Performance is suitably measured against four criteria that users have identified as key for neuroprosthetic use: accuracy, speed, multi-functionality, and minimal calibration. Accuracy can be measured as percent correct classification, with secondary metrics of sensitivity and specificity.

Response time can be measured as time difference between the cue presentation for each movement and associated decoder response. Multi-functionality can be measured by the number of movements that can accurately (>90%) be decoded in a single session. Calibration time can be measured as time spent calibrating both the decoding algorithms and the stimulation parameters. The first time a participant uses the FES sleeve, a trained operator suitably performs guided trial-and-error calibration to map stimulation parameters to the desired movements. After the initial calibration, we have observed that stimulation parameters are mostly stable from day-to-day. However, due to variation in sleeve placement or gradual changes in the arm, occasional recalibration may be needed. In this case, we will use an auto-calibration process to automatically update the mapping from electrodes to muscle activation for different hand movements, for example via a class of genetic algorithm known as differential evolution (DE). This optimization procedure efficiently selects stimulation parameters and adapts based on sensor feedback to minimize the distance of actual hand position relative to a target position. Our preliminary results show that this approach will allow for fast and automated stimulation recalibration when needed (refer to FIG. 6). By such approaches, it is expected that the ReGrasp system can be a take-home device provided with a robust suite of algorithms for calibration and control of the take-home ReGrasp device.

In some contemplated embodiments, EMG training and FES conditioning is performed, for example to train participants to use the ReGrasp system and establish baseline performance benchmarks, including scores on standardized tasks and MU activity (without the use of the system). In a suitable approach, the participants are first trained to use the system to improve voluntary control of EMG signals. Training can be performed with a computer-based simulation in which subjects control an avatar of the hand/arm displayed on a visual display. The training period can also be used to condition the muscles for FES. In one example, we can test and validate the decoding methods to isolate four attempted hand movements (i.e., hand open, power grip, lateral pinch, and tip-to-tip pinch grips). We can also analyze and decompose EMG signals, collected without FES, to extract MU activity using methods as described in Aim 1.3 and establish benchmarks for MU-based tracking of corticospinal reorganization or neuroplasticity. At the end of the training, it is expected that participants will be able to use the system to reanimate those four basic hand functions that are essential for accomplishing ADLs (e.g., grooming, self-feeding). We also expect to identify electrode patterns that are needed for EMG decoding as well as FES, including optimization of FES parameters (e.g., stimulation amplitude, waveform, frequency, electrode patterns) and automate procedures for calibrating the FES controller and decoding algorithms. Still further, baseline performance benchmarks can be established for each participant. These baseline benchmarks can suitably include MU activity information for each hand movement (e.g., total number of MUs, task-specific recruitment properties), baseline scores on GRT without the use of FES (e.g., number of transfers, transfer times), and decoder performance (e.g., accuracy, response time).

Figure 12:
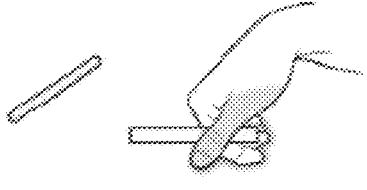
FIG. 12 diagrammatically illustrates six GRT objects and the hand-open function that the participants are expected to use during training.

In further aspects, effectiveness of the ReGrasp system is evaluated in improving hand function during in-clinic testing, for example to evaluate the safety and feasibility (i.e., reliability, effectiveness, and ease-of use) of the ReGrasp system with SCI participants in the lab. It is expected that: (1) individuals with tetraplegia from SCI will be able to safely use the ReGrasp system in the lab; (2) the system will be easy and intuitive to use and will enable users to grasp and manipulate Grasp and Release Test (GRT) objects (e.g., see FIG. 12 which illustrates six GRT objects and the hand-open function that the participants are expected to use during training); and (3) users will report favorable attitudes toward the device on a Psychosocial Impact of Assistive Device Scale (PIADS). In a contemplated approach, EMG signal quality in the presence of FES is first assessed, and the FES artifact removal methods optimized starting with the methods used to remove artifacts in our ReGrasp v1 clinical trial. Next, the decoding methods are optimized for data contaminated with FES induced artifacts to isolate and control the four hand movements with high (>90%) accuracy. EMG signals, collected without FES, are also analyzed to extract MU activity for longitudinal tracking of neuroplastic changes in task-specific MU recruitment. Mounting and setup of the device on the powerchair 44 is adjusted to accommodate the user as needed. Then, the user's ability to grasp GRT objects (i.e., fork, can, block, paperweight, peg) is verified and object manipulation skills are quantified on the GRT. Signal quality, GRT performance data, and safety data (adverse event logs) may be collected. Additionally, participants may provide feedback via PIADS at the end of lab testing regarding device design and likelihood of using such a system in their daily life. Outcome measures may suitably include: (1) safety: adverse event (AE) reports; (2) feasibility (performance): GRT item scores, decoder accuracy, MU tracking, setup time; and feasibility (end-user ratings) with open-ended design feedback from end-users and psychosocial impact of the device on the PIADS. The GRT is a suitable test because it assesses common grips for items that vary in size and weight, and is a measure used in prior neuroprosthetic trials. The PIADS was chosen because of its rigor, acceptance within the assistive device community as being predictive of device adoption, and patient-centered focus. The disclosed approach provides rigorous safety and performance testing and enables demonstration of feasibility for the system in the target clinical population. The fully wearable ReGrasp system is expected to be safe (i.e., no serious, device-related AE); feasible for participants to use for functional object manipulation in the lab, and favorably evaluated on the PIADS.

Figure 13:
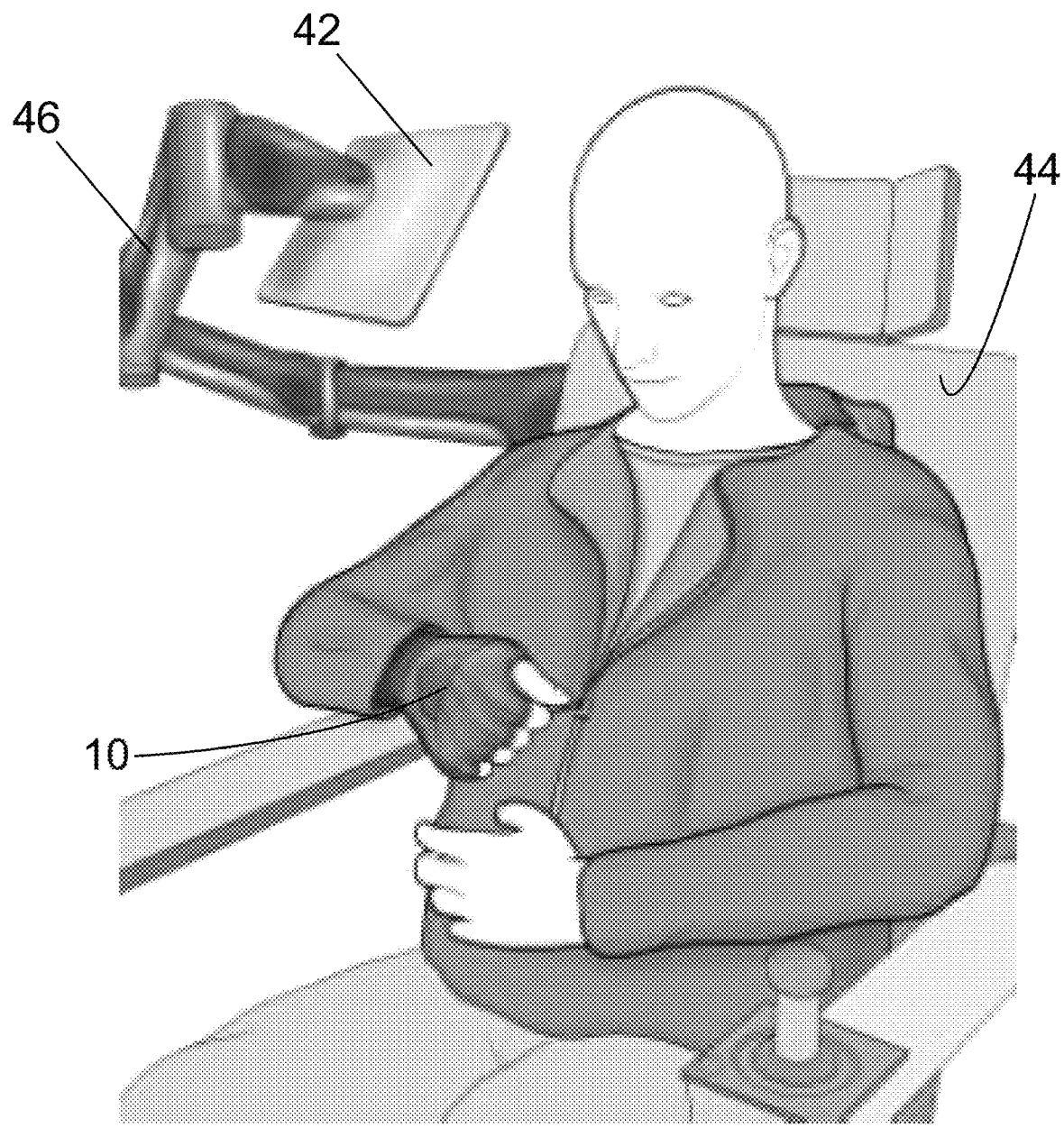
FIG. 13 diagrammatically illustrates an Arm Motor and Ability Test (AMAT) dressing task.
Figure 14:
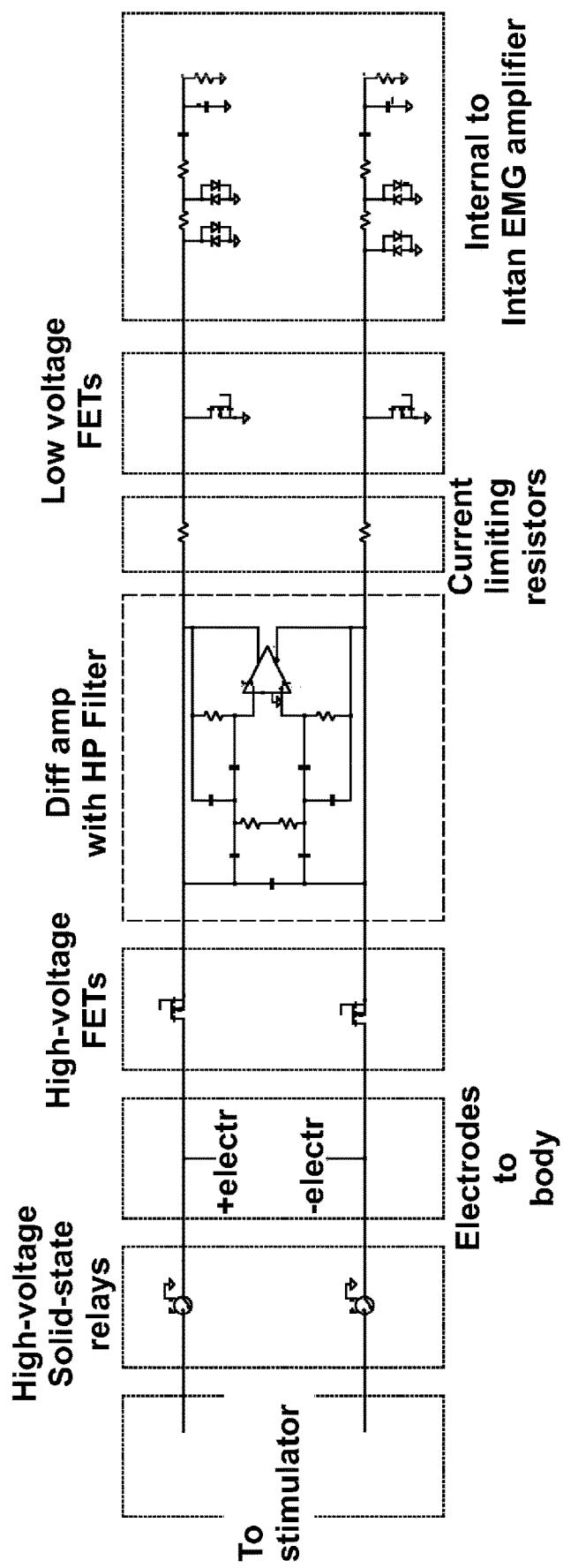
FIG. 14 present an illustrative embodiment of a suitable circuit for the FES/EMG electronics of the ReGrasp v2 system of FIG. 11.

To evaluate efficacy of the ReGrasp system for performing self-care tasks at home and to assess the impact of restored function on psychosocial outcomes, the following hypotheses can be tested, namely that: (1) manual dexterity will be better than baseline using the ReGrasp system; (2) the ability to perform ADLs will be positively impacted by ReGrasp use in the home; and (3) maximizing upper limb function with ReGrasp system in the home will positively impact quality of life and perceived level of disability. In one suitable method, a series of clinically relevant, psychometrically validated, and reliable standardized tests may be used to assess the impact of the ReGrasp system on different aspects of the user's daily lives. Unfortunately, there is no single consensus framework for evaluating neuroprosthetics; therefore, several different instruments can be leveraged to evaluate different aspects of system use. To evaluate changes in manual dexterity and upper limb motor function, the GRASSP114 can be used, which is a validated metric specifically designed for quantifying and tracking changes in arm and hand function after SCI. To evaluate whether the system improves the user's ability to complete ADL-like tasks such as feeding and grooming, the Arm Motor and Ability Test (AMAT) can be used (see, e.g. FIG. 13 which shows an AMAT dressing task), which enables quantification of the performance and movement quality of the illustrative 13 ADLs. In addition, Goal Attainment Scaling (GAS) can be used to quantify performance changes for tasks that are functional and meaningful specifically to an individual. A study therapist suitably works with the participant to identify goals and set quantitative success criteria for self-selected ADLs. Finally, perceived psychosocial changes using the Quality of Life in Neurological Disorders (Neuro-QOL) are assessed. The number, quality, and amplitude of MU activity throughout the duration of the study can also be assessed.

Figure 15:
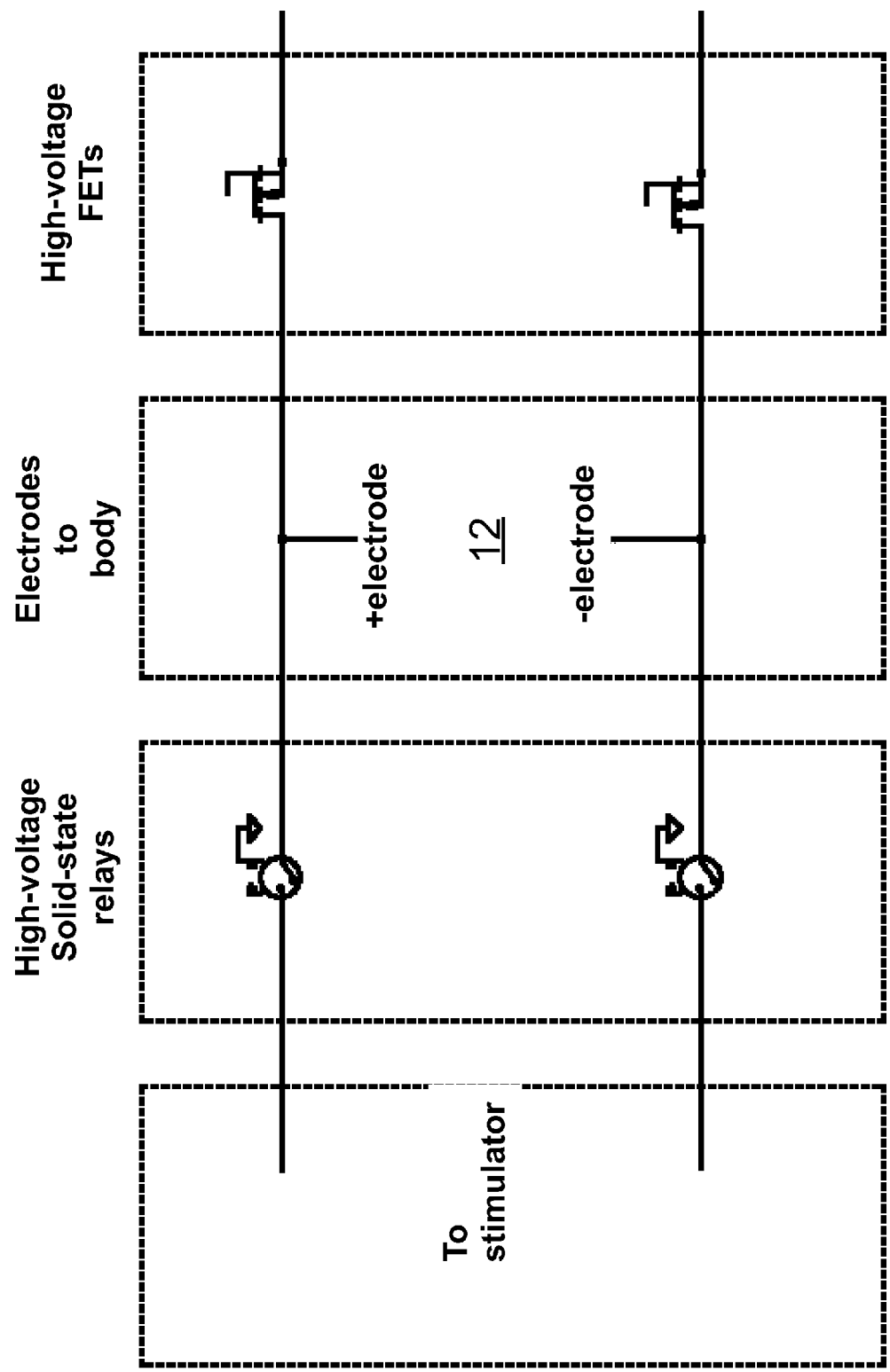
FIGS. 15, 16, and 17 present enlarged views of portions of the circuit of FIG. 14.
Figure 16:
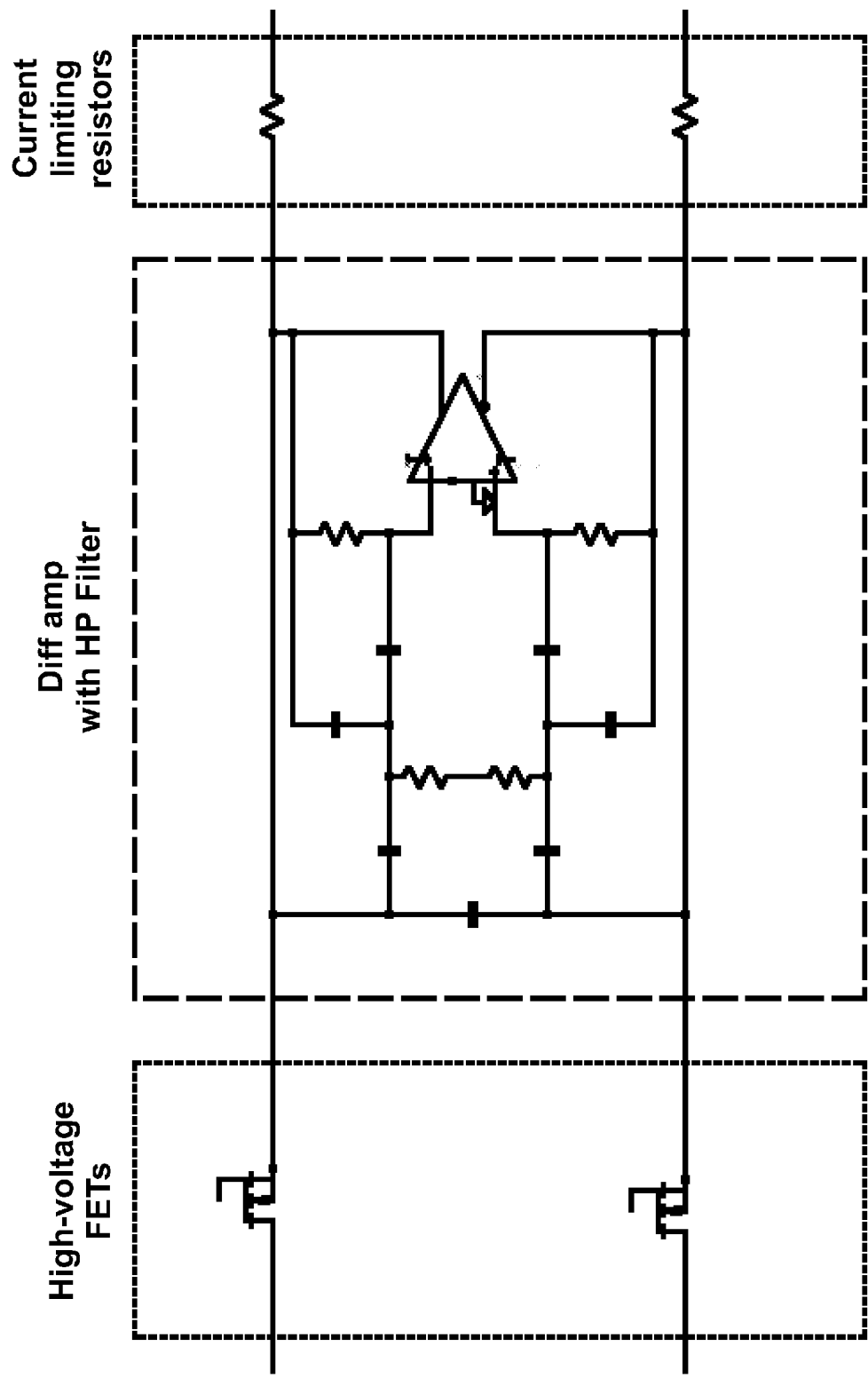
Figure 17:
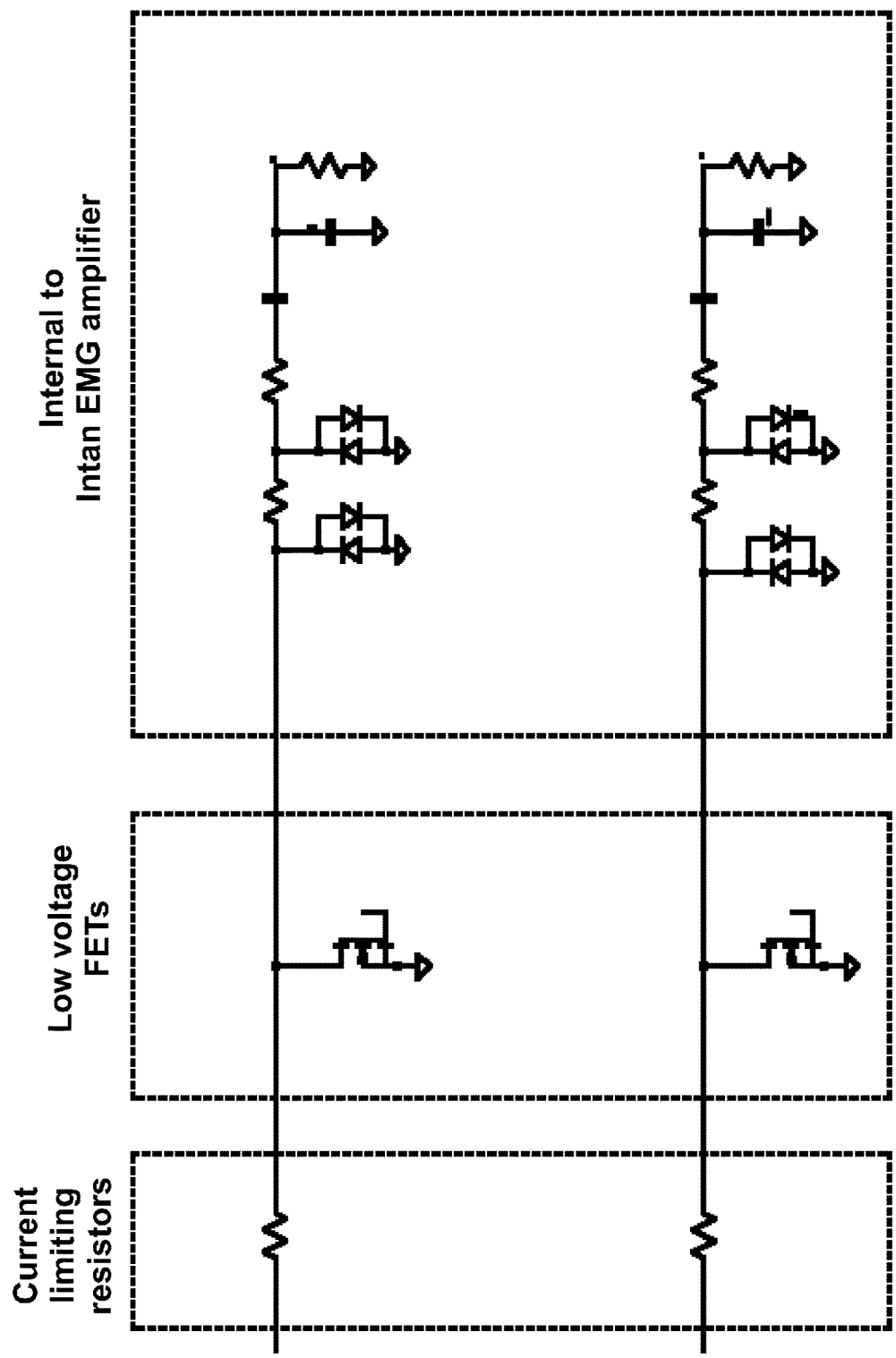

With reference to FIG. 14-17, an illustrative embodiment of a suitable circuit for the FES/EMG electronics 40 is shown. It is noted that FIGS. 15, 16, and 17 illustrate the same electronic circuit as FIG. 14, but enlarged and with some overlap between the sub-circuits shown in FIGS. 15, 16, and 17 to indicate the continuity. Specifically, FIG. 15 is cut off at the right side and connects with FIG. 16 with some overlap, FIG. 16 shows the central differential amplifier section, and FIG. 17 is cut off at the left side and connects with FIG. 16 again with some overlap.

The illustrative drive/control electronic circuit of FIGS. 14-17 provides for both EMG readout and electrical stimulation for FES. The electrodes 12 are diagrammatically indicated in FIG. 12. The sections of the circuit to the left of the electrodes 12, best seen in FIG. 15, correspond to the stimulation hardware. In one contemplated embodiment, these sections are not included in the FES/EMG electronics 40 but rather are integrated into the integrated EMG amplifiers 30 of the sleeve 10 (see FIG. 10). The sections to the right of the electrodes 12, best seen in FIGS. 16 and 17, comprise EMG readout hardware. In one contemplated embodiment, portions of these sections are implemented as an Intan EMG amplifier (available from Intan Technologies, Los Angeles, Calif., USA). This is merely an illustrative example.

During FES stimulation, the high voltage solid state relays (best seen in FIG. 15) are closed to connect the stimulator to the electrodes 12, and the high voltage FETs (i.e. field-effect transistors, best seen in FIGS. 15 and 16) are off to protect the EMG readout circuitry from the high voltages applied to the electrodes 12 by the stimulator (e.g. on the order of 100-200 volts or higher for some FES applications). The low voltage FETs (best seen in FIG. 17) may also be on to pull the connected lines to ground to block any residual stimulation passing through the off high voltage FETs to further protect the EMG amplifier.

During EMG readout, the high voltage FETs are on and the low voltage FETs are off in order on to provide electrical continuity between the electrodes 12 and the EMG amplifier. The differential amplifier with high pass filter (best seen in FIG. 16) is an optional component, but provides faster switching between the stimulation and EMG readout phases and to remove common mode noise.

Figure 18:
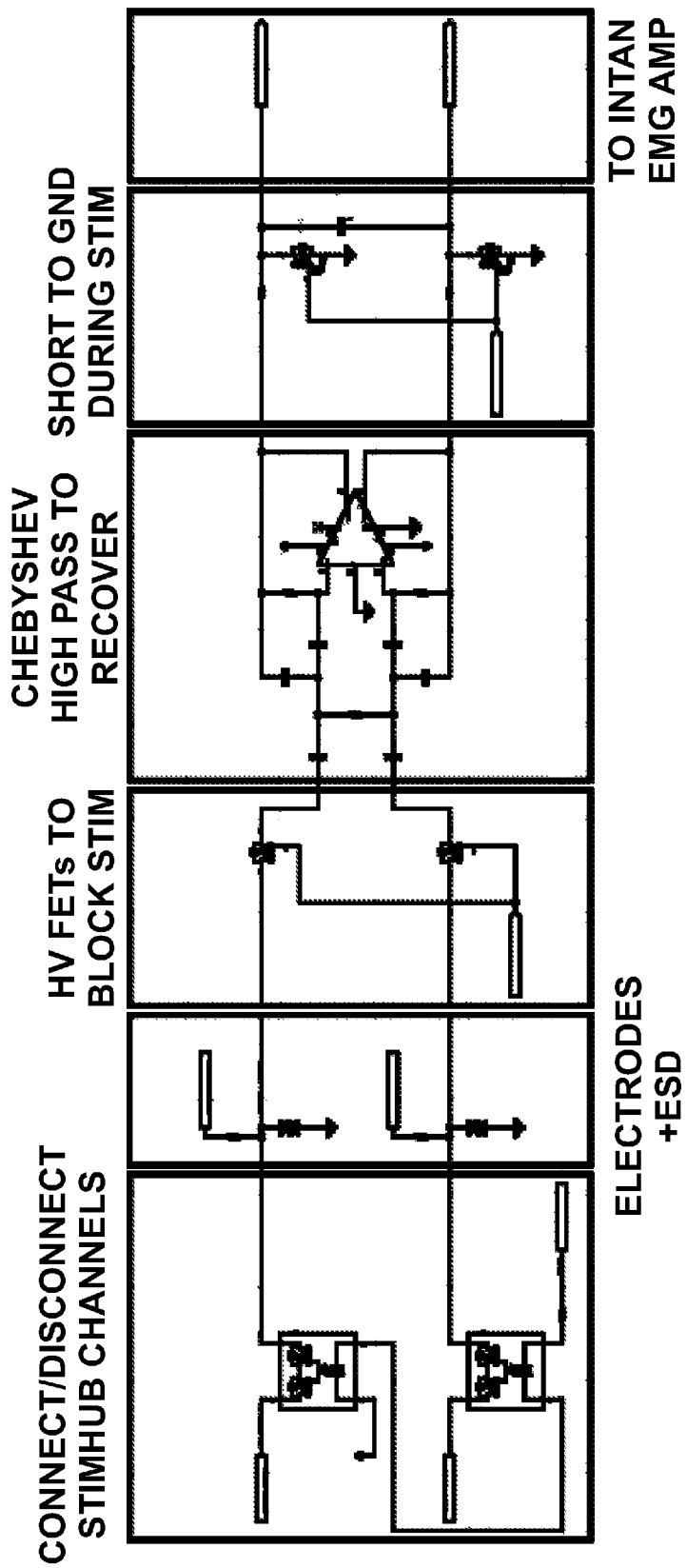
FIG. 18 presents another illustrative embodiment of a suitable circuit for the FES/EMG electronics of the ReGrasp v2 system of FIG. 11, along with examples of relative timing of the control signals.

FIG. 18 presents another illustrative embodiment of a suitable circuit for the FES/EMG electronics of the ReGrasp v2 system of FIG. 11, including some ancillary connections indicated and shown along with examples of relative timing of the control signals.

The preferred embodiments have been illustrated and described. Obviously, modifications and alterations will occur to others upon reading and understanding the preceding detailed description. It is intended that the invention be construed as including all such modifications and alterations insofar as they come within the scope of the appended claims or the equivalents thereof.

The invention claimed is:

1. A portable and wearable hand-grasp neuro-orthosis configured for use in a home environment to restore volitionally controlled grasp functions for a subject with a cervical spinal cord injury (SCI), comprising:
    a wearable sleeve with electrodes;
    electromyography (EMG) amplifiers integrated with the wearable sleeve and configured to record and digitize EMG signals acquired via the electrodes, the EMG amplifiers integrated with the wearable sleeve including switches that automatically disconnect and reconnect the EMG amplifiers;
    electronics for operating the wearable sleeve to perform functional electrical stimulation (FES) and EMG, the electronics configured for mounting on a wheelchair, the electronics configured to generate a sync output to automatically operate the switches of the EMG amplifiers to disconnect the EMG amplifiers from the electrodes before FES is applied and to reconnect the EMG amplifiers with the electrodes after the FES is applied; and
    a controller configured for mounting on a wheelchair and controlling the electronics to read EMG via the EMG amplifiers integrated with the sleeve, decode the read EMG to determine an intent of the user, and operate the electronics to apply FES via the sleeve to implement the intent of the user.

2. The portable and wearable hand-grasp neuro-orthosis of claim 1 wherein the controller performs electromyography (EMG) controlled functional electrical stimulation (FES) using the electronics and the sleeve.

3. The portable and wearable hand-grasp neuro-orthosis of claim 2 wherein the controller decomposes EMG signals received from the electrodes of the sleeve by motor unit (MU) decomposition to identify MU action potential (AP) characteristics of the EMG signals.

4. The portable and wearable hand-grasp neuro-orthosis of claim 1 wherein the neuro-orthosis restores hand function.

5. The portable and wearable hand-grasp neuro-orthosis of claim 1 wherein the neuro-orthosis decodes the read EMG signals to detect the intent of the user comprising an attempted hand movement.

6. The portable and wearable hand-grasp neuro-orthosis of claim 1 wherein the electrodes of the sleeve comprise non-invasive high density electromyography (HD-EMG) surface electrodes.

7. The portable and wearable hand-grasp neuro-orthosis of claim 6 wherein the electronics include a portable FES stimulator with at least 100 channels.

8. The portable and wearable hand-grasp neuro-orthosis of claim 1 wherein the controller includes a display arranged to be viewed by the subject and programmed to present an avatar of at least the hand.

9. The portable and wearable hand-grasp neuro-orthosis of claim 8 further comprising an articulated arm attachable to a wheelchair via which the controller including the display is mounted in a position viewable by the subject when the subject is in the wheelchair.

10. The portable and wearable hand-grasp neuro-orthosis of claim 9 wherein the controller including the display comprises a tablet computer.

11. A portable and wearable hand-grasp neuro-orthosis configured for use in a home environment to restore volitionally controlled grasp functions for a subject with a cervical spinal cord injury (SCI), comprising:

a wheelchair;

a wearable sleeve with electrodes and electromyography (EMG) amplifiers integrated with the wearable sleeve and configured to record and digitize EMG signals acquired via the electrodes, the EMG amplifiers including switches operative to disconnect the EMG amplifiers from the electrodes and to reconnect the EMG amplifiers with the electrodes;

electronics for operating the wearable sleeve to perform functional electrical stimulation (FES) and EMG, the electronics mounted on the wheelchair, the electronics configured to generate a sync output that automatically operates the switches of the EMG amplifiers to disconnect the EMG amplifiers from the electrodes before FES is applied via the sleeve and to reconnect the EMG amplifiers with the electrodes after the FES is applied; and a controller mounted on the wheelchair and controlling the electronics.

12. The portable and wearable hand-grasp neuro-orthosis of claim 11 wherein the controller decomposes EMG signals received from the electrodes of the sleeve by motor unit (MU) decomposition to identify MU action potential (AP) characteristics of the EMG signals.

13. The portable and wearable hand-grasp neuro-orthosis of claim 11 wherein the neuro-orthosis restores hand function.

14. The portable and wearable hand-grasp neuro-orthosis of claim 11 wherein the neuro-orthosis decodes EMG signals to detect attempted hand movements.

15. The portable and wearable hand-grasp neuro-orthosis of claim 11 wherein the electrodes of the sleeve comprise non-invasive high density electromyography (HD-EMG) surface electrodes.

16. The portable and wearable hand-grasp neuro-orthosis of claim 15 wherein the electronics include a portable FES stimulator with at least 100 channels.

17. The portable and wearable hand-grasp neuro-orthosis of claim 11 wherein the controller includes a display arranged to be viewed by the subject.

18. The portable and wearable hand-grasp neuro-orthosis of claim 17 further comprising an articulated arm connecting the controller including the display to the wheelchair with the display in a position viewable by the subject when the subject is in the wheelchair.

* * * * *